US005840728A

United States Patent [19]

Marquez et al.

[11] Patent Number: 5,840,728
[45] Date of Patent: Nov. 24, 1998

[54] CONFORMATIONALLY LOCKED NUCLEOSIDE ANALOGS AS ANTIHERPETIC AGENTS

[75] Inventors: Victor E. Marquez, Gaithersburg; Marc C. Nicklaus, Elkridge; Joseph J. Barchi, Jr., Bethesda, all of Md.; Juan B. Rodriguez, Buenos Aires, Argentina; Maqbool Siddiqui, Rockville, Md.

[73] Assignee: United States of America as represented by the Department of Health and Human services, Washington, D.C.

[21] Appl. No.: 908,724

[22] Filed: Aug. 7, 1997

Related U.S. Application Data

[60] Provisional application No. 60/023,565 Aug. 7, 1996.
[51] Int. Cl.⁶ ..................... A61K 31/44; A61K 31/505; A61K 31/32; C07D 239/24
[52] U.S. Cl. ................. 514/261; 514/269; 544/242; 544/264
[58] Field of Search ...................... 514/261, 269; 544/242, 264

[56] References Cited

U.S. PATENT DOCUMENTS 5,629,454  5/1997  Marquez et al. .................. 568/327

OTHER PUBLICATIONS

K. Altmann, et al., "4',6'–Methano Carbocyclic Thymidine: A Conformationally Constrained Building Block for Oligonucleotides," *Tetrahedron Letters*, 35(15):2331–2334 (1994).
K. Altmann, et al., "1'6'–Methano Carbocyclic Thymidine: Synthesis, X–ray Crystal Structure, and Effect on Nucleic Acid Duplex Stability," *Tetrahedron Letters*, 35(41):7625–7628 (1994).
C. Altona, et al., "Conformationally Analysis of the Sugar Ring in Nucleosides and Nucleotides. A New Description Using the Concept of Pseudorotation," *Jour. American Chem. Society*, 94(23):8205–8212 (1972).
K.A. Cruickshank, et al., "The Benzoylation of Uracil and Thymine," *Tetrahedron Letters*, 25(6):681–684 (1984).
K.J. Divakar, et al., "4–(1,2,4–Triazol–1–yl)– and 4–(3–Nitro–1,2,4–triazol–1–yl)–1–(β–D–2,3,5–tri–O–acetylarabinofuranosyl) pyrimidin–2 (1H)–ones. Valuable Intermediates in the Synthesis of Derivatives of 1–(β–D–Arabinofuranosyl) cytosine (Ara–C)," *J. Chem. Soc. Perkin Trans.* 1:1171–1176 (1982).
F.G. Hayden, et al., "Antiviral Agents," *Basic Principles in the Diagnosis and Management of Infectious Diseases* Chapter 31, pp. 270–286.

B. Jagannadh, et al., "¹H NMR Study of the Sugar Pucker of 2',3'–Dideoxynucleosides with Anti–Human Immunodeficiency Virus (HIV) Activity," *Biochem. and Biophys. Res. Communications* 179(1):386–391 (1991).
V.E. Marquez, et al., "Total Synthesis of (−)–Neplanocin A," *J. Org. Chem.* 53:5709–5714 (1988).
R. Marumoto, et al., "Synthesis of Aristeromycin Analogs," *Chem. Pharm. Bull.* 24(11):2624–2628 (1976).
O. Mitsunobu, "The Use of Diethyl Azodicarboxylate and Triphenylphosphine in Synthesis and Transformation of Natural Products," *Synthesis* 1:1–28 (1981).
Physicians' Desk Reference, 47th Edition, pp. 844–850 (1993).
J. Plavec, et al., "Structural analysis of 2',3'–dideoxyinosine, 2',3'–dideoxyadenosine, 2',3'–dideoxyguanosine and 2',3'–dideoxycytidine by 500–MHz 1H–NMR spectroscopy and ab–initio molecular orbital calculations," *Journal of Biochemical and Biophysical Methods* 25:253–272 (1992).
J. Rodriguez, et al., "Synthesis of Cyclopropane–fused Dideoxycarbocyclic Nucleosides Structurally Related to Neplanocin C," *Tetrahedron Letters* 34(39):6233–6236 (1993).
J. Rodriguez, et al., "Conformationally Locked Nucleoside Analogues. Synthesis of Dideoxycarbocyclic Nucleoside Analogues Structurally Related to Neplanocin C," *J. Med. Chem.* 37:3389–3399 (1994).
W. Saenger, "Structures and Conformational Properties of Bases, Furanose Sugars, and Phosphate Groups," *Principles of Nucleic Acid Structure*, Springer–Verlag, New York, pp. 51–104 (1984).
Y.F. Shealy, et al., "Carbocyclic Analogs of 2'–Deoxyadenosine and 3'–Deoxyadenosine," *Tetrahedron Letters* 27:2231–2234 (1969).
S. Takano, et al., "Regioselective Formation of 3–tertalkoxy–1,2–Glycols from 2,3–0–Alkylidenetriols with Trimethylaluminum," *Tetrahedron Letters* 29(15):1823–1824 (1988).
E.W. Taylor, et al., "A stereochemical rationale for the activity of anti–HIV nucleosides," *Antiviral Chemistry & Chemotherapy* 1(3):163–173 (1990).
P. Van Roey, et al., "Correlation of Molecular Conformation and Activity of Reverse Transcriptase Inhibitors," *Ann. NY Acad. Sci.* 616:29–40 (1990).

*Primary Examiner*—Gary L. Kunz
*Attorney, Agent, or Firm*—Knobbe, Martens, Olson & Bear, LLP

[57] ABSTRACT

A method for treatment of herpes virus infection by administering an effective virus-inhibiting amount of a cyclopropanated carbocyclic 2'-deoxynucleoside to an individual in need thereof. The nucleoside analogs are effective against herpes simplex virus types 1 and 2; Epstein-Barr Virus and human cytomegalovirus.

5 Claims, 6 Drawing Sheets

CONFORMATIONALLY LOCKED NUCLEOSIDE ANALOGS AS ANTIHERPETIC AGENTS

CROSS-REFERENCE TO RELATED APPLICATIONS

This application claims priority under 35 U.S.C. §119(e) to U.S. Provisional application Ser. No. 60/023,565, filed Aug. 7, 1996.

FIELD OF THE INVENTION

The present invention relates to the use of conformationally locked nucleosicle analogs as antiviral agents. More specifically, the invention relates to the use of 2'-deoxynucleoside analogs locked in the Northern conformation as antiherpetic agents.

BACKGROUND OF THE INVENTION

Nucleoside analogs lacking 2'- and 3'-hydroxyl groups (dideoxynucleosides), as well as those 2'-deoxynucleosides where the 3'-hydroxyl function has been chemically modified or changed, can function as chain terminators of DNA synthesis after their incorporation into DNA. This is the basis of the Sanger dideoxynucleotide method for DNA sequencing (Sanger et al., Proc. Natl. Acad. Sci. USA, 1977). Intense effort has focused on the design and use of these compounds as inhibitors of viral replication (Van Roey et al., Ann. N.Y Acad. Sci, 616:29, 1990). Although the conformation of the sugar moiety in these analogs is believed to play a critical role in modulating biological activity, including the anti-HIV activity mediated by derivatives such as azidothymidine (AZT) and dideoxyinosine (ddI), the main problem encountered in correlating a specific type of sugar conformation with the biological activity of nucleoside analogs is that the sugar ring is quite flexible and its conformation in solution can differ markedly from its conformation in the solid state (Jagannadh et al., Biochem. Biophys. Res. Commun., 179:386; Plavec et al., Biochem. Biophys. Methods, 25:253). Thus, for nucleosides in general, any structure-activity analysis which is based solely on the solid-state conformation would be inaccurate unless it was previously determined that both solution and solid-state conformations were the same.

In solution there is a dynamic equilibrium between Northern (N) and Southern (S) type furanose conformers (Taylor et al., Antiviral Chem. Chemother., 1:163–173, 1990) as defined in the pseudorotational cycle (FIG. 1). In this cycle, an absolute Northern conformation would correspond to a range of P (angle of pseudorotation) between 342° and 18° ($_2E \rightarrow ^3T_2 \rightarrow ^3E$), whereas an absolute Southern conformation would be defined when P is 162°–198° ($^2E \rightarrow ^2T_3 \rightarrow _3E$). Preference for any of these specific conformations in solution is determined by the interplay of important interactions resulting from anomeric and gauche effects (Saenger, in Principles of Nucleic Acid Structure, Springer-Verlag, New York, pp. 51–104, 1984; Plavec et al., J Am. Chem. Soc., 94:8205–8212, 1972). When a nucleoside or nucleotide binds to its target enzyme, only one form is expected to be present at the active site. While the energy gap between Northern and Southern conformations is about 4 kcal/mol, such a disparity can explain the difference between micromolar and nanomolar binding affinities.

The conformations of nucleosides and their analogs can be described by the geometry of the glycosyl link (syn or anti), the rotation about the exocyclic C4'–C5' bond and the puckering of the sugar ring leading to formation of the twist and envelope conformations. Two types of sugar puckering are generally energetically preferred, namely the C2'-exo/C3'-endo (N or Northern) and the C2'-endo/C3'-exo (S or Southern). The endo and exo refer to displacement of the atom above or below the plane of the ribose ring, respectively. The torsion angles $\chi$ [C2-N1-C1'-O4' (pyrimidines) or C4-N9-C1'-O4' (purines)] and $\gamma$ (C3'-C4'-C5'-O5') describe, respectively, the orientations of the base and the 5'-hydroxyl group relative to the ribose ring.

In DNA duplexes, a Southern conformation of the repeating nucleoside unit confers upon the double helix a B-conformation, whereas the Northern conformation induces an A-conformation double helix. The A and B forms of DNA differ in the number of base pairs per turn, the amount of rotation per base pair, the vertical rise per base pair and the helical diameter. In addition, in stretches of DNA containing alternating purines and pyrimidines, a left-handed helix called Z-DNA may form.

Altmann et al. (Tetrahedron Lett., 35:2331–2334, 1994) demonstrated that substitution of N-methanocarba-thymidine (N-methanocarba-T) for thymidine in DNA/RNA heteroduplexes increased the thermodynamic stability of the double helix, as indicated by a positive increase in the $T_m$, whereas the Southern conformer induced a small destabilizing effect (Altmann et al., Tetrahedron Lett., 35:7625–7628, 1994). The increased thermal stability reported for two different N)-methanocarba-T-containing oligodeoxynucleotides (ODNs) versus conventional ODNs was between 0.8 and 2.1° for a single modified nucleotide; however, no data was reported for an CDN containing multiple (N)-methanocarba-Ts.

The conformationally (Northern) locked nucleoside analogs for use in the present invention are described in copending U.S. Pat. No. 5,629,454 and in Published International Application No. PCT W095/08541.

There is a constant need for effective antiherpetic agents. The present invention provides such agents.

SUMMARY OF THE INVENTION

One embodiment of the present invention is a method of treating a herpes virus infection in an individual in need thereof, comprising the step of administering to said individual an effective herpes antiviral amount of a compound having the formula

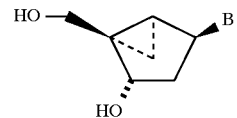

or a substituted derivative thereof in a pharmaceutically acceptable carrier, said compound locked in the Northern conformation, wherein B is adenine, thymine, cytosine or guanine. According to one aspect of this preferred embodiment, the herpes virus is Herpes Simplex Virus-1, Herpes Simplex Virus-2, Epstein-Barr Virus, Cytomegalovirus or Varicella-Zoster Virus. Preferably, the effective amount is between about 300 mg and about 15,000 mg per day. Advantageously, the administering step is topical, oral, intravenous, intramuscular or subcutaneous.

Another embodiment of the invention is a pharmaceutical composition comprising the compound shown above in a pharmaceutically acceptable carrier. Preferably, the carrier is a sterile carrier suitable for parenteral administration.

Alternatively, the carrier is suitable for topical administration. Further, the carrier may also be suitable for oral administration.

The present invention also provide an oligodeoxynucleotide or phosphorothioate derivative thereof comprising at least one deoxynucleoside analog having the formula shown above.

DETAILED DESCRIPTION OF THE PREFERRED EMBODIMENTS

Figure 1:
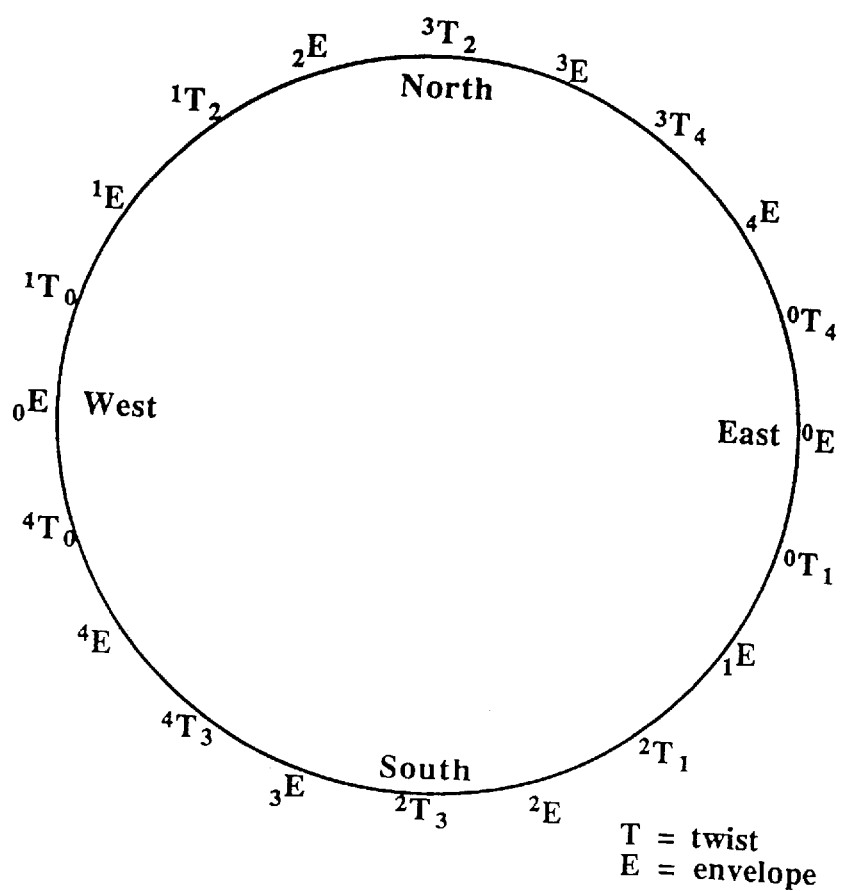
FIG. 1 illustrates the pseudorotational cycle.
Figure 2:
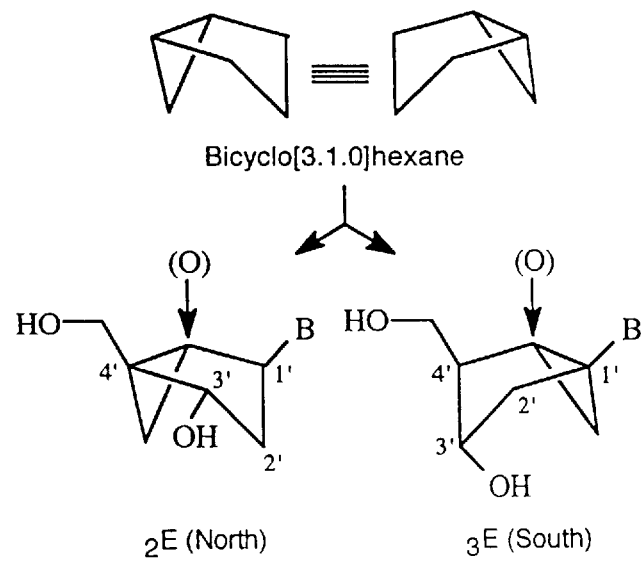
FIG. 2 illustrates the placement of substituents on the Bicyclo[3.1.0]hexane template for generating the Northern and Southern 2'-methanocarba deoxynucleoside analogs.

The present invention includes the observation that carbocyclic 2'-deoxynucleoside analogs locked in the Northern conformation are effective antiherpetic agents. These compounds are described in copending U.S. application Ser. No. 08/311,425 and in PCT publication W095/08541, the entire contents of which are hereby incorporated by reference. Conformationally rigid (locked) nucleoside analogs are constructed on a bicyclo[3.1.0]hexane template whose value of P (pseudorotational angle) fits within the range of absolute Northern or Southern conformations. This bicyclo[3.1.0] hexane template exists exclusively as a pseudoboat, and carbocyclic nucleosides built thereon can adopt either a Northern or Southern conformation depending on the relative disposition of substituents on the ring (FIG. 2). Thus, a Northern C2'-exo (2E) envelope conformation is obtained when the cyclopropane ring was fused between carbon C4' and the carbon supplanting the ribofuranoside oxygen, Conversely, fusion of the cyclopropane ring between carbon C1' and the carbon supplanting the ribofuranoside oxygen provides the opposite Southern conformation.

The carbocyclic 2'-deoxynucleoside analogs are referred to herein as (N)-2'-deoxy-methanbcarba-A (adenosine analog), (N)-methanocarba-T (thymidine analog), (N)-2'-deoxy-methanocarba-G (guanosine analog), (N)-2'-deoxy-methanocarba-C (cytosine analog) and (N)-2'-deoxy-methanocarba-U (uridine analog). The structure of these analogs is indicated below (B=adenine, thymine, cytosine, guanine or uracil).

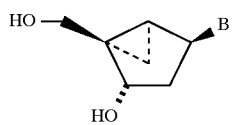

(N)-2'-deoxy-methanocarba-nucleoside analogs effectively inhibit viral plaque formation in human foreskin fibroblasts (HFF) by Herpes Simplex virus Types I and II (HSV-1 and HSV-2), Epstein-Barr Virus (EBV) and Human Cytomegalovirus (CMV), all members of the Herpesviridae family. N-methanocarba-T is effective against HSV-1, HSV-2 and EBV. (N)-methanocarba-A exhibited antiviral effects against Human CMV, EBV and HSV-2. HSV-1 and HSV-2 cause oral (fever blisters) and genital herpes simplex lesions, respectively; however, HSV- 1 is the causative agent in approximately 5% of genital herpes cases. HSV-2 infection may lead to cervical cancer. CMV infection leads to cytomegalic inclusion disease (CMV). EBV is the causative agent of Burkitt's lymphoma and mononucleosis. Other members of the Herpesviridae family include Varicella-Zoster Virus (VZV), the causative agent of chicken pox and shingles. Herpes virus infections can also lead to Herpes Zoster. It is contemplated that the nucleoside analogs described herein may be used to treat any condition caused by a herpes virus.

The synthesis of the (N)-methanocarba-adenosine, guanine, cytidine, thymidine and uridine analogs is described in the examples presented below and in Schemes 1–4. The antiherpetic effect of various substituted derivatives of the (N)-methanocarba 2'-deoxynucleoside analogs described below can easily be determined by one of ordinary skill in the art using the human foreskin fibroblast (HFF) assay described herein without undue experimentation.

2'-deoxyaristeromycin, the corresponding non-rigid analog of (N)-methanocarba-adenosine, was first synthesized as a racemic mixture (Shealy et al., Tetrahedron Lett., 2231, 1969), then in enantiomerically pure form (Marumoto et al., Chem. Pharm. Bull., 24:2624, 1976). No biological activity has been reported for this compound. In contrast, the (N)-locked analog (compound 4) is active against HSV-2, HCMV and EBV (Table 3). Several adenosine analogs active against HCMV are also good inhibitors of the enzyme S-adenosylhomocysteine hydrolase (Ado-Hcy-ase). The activity of (N)-methanocarba-A (4) against AdoHcy-ase is very low, exhibiting only 20% inhibition at 100 FM concentration, indicating that the antiviral activity of the adenosine analog is independent of its interaction with this enzyme.

In Schemes 1–2, synthesis of intermediate 12 represents a significant improvement over previous syntheses for two reasons: 1) compound 12 is chiral, so there is no need for optical resolution at the end of the synthesis, and 2) compound 12 represents a universal starting material for the synthesis of related carbocyclic 2'-deoxynucleoside analogs. Cyclopentenol 6 is obtained from the sodium borohydride reduction of cyclopentenone 5 (Marquez et al., J. Org. Chem., 53:5709, 1988), the entire contents of which are hereby incorporated by reference. Regioselective cleavage of the contiguous O-isopropylidenetriol system in 6 with trimethylaluminum (Takano et al., Tetrahedron Lett., 29:1823, 1988) produces the corresponding carbocyclic 3-tert-butoxy-1,5-glycol 7, which in the presence of tert-butyldirnethylsilyl chloride reacts exclusively at the less hindered allylic alcohol position to give the protected intermediate 8. Barton's radical deoxygenation of 8 at C-5 occurs via the xanthate 9 in the presence of AIBN to give compound 10. Deprotection of the silyl ether in 10 by fluoride ion unmasks the hydroxyl group (compound 11) which directs the ensuing cyclopropanation to give compound 12. This compound is directly coupled to 6-chloropurine under Mitsunobu conditions (Mitsunobu, Synthesis, 1:1–28, 1981) to give the protected carbocyclic nucleoside intermediate 13. Following aminolysis of 13 with ammonia, and the simultaneous removal of both benzyl and tert-butyl groups, the (N)-2'-deoxy-methanocarba adenosine derivative 4 is obtained.

For the pyrimidine derivatives (Scheme 3), protected $N^3$-benzoylthymine and $N^3$-benzoyluracil (Cruickshank et al., Tetrahedron Lett., 25:681, 1994) are coupled according to Scheme 3. In the case of 16, the O-alkylated product predominates, whereas for the uracil analog 17, the situation is reversed. Base-catalyzed deprotection of the N-benzoyl group from intermediates 16 and 17 yields the penultimate intermediates 18 and 19, respectively, and simultaneous removal of both O-benzyl and O-tert-butyl groups with $BCl_3$ provide the desired targets (N)-methanocarba-T (20) and N-methanocarba-U (21). (N)-methanocarba-C (22) is prepared from (N)-methanocarba-U via formation of the triazole intermediate as described (Divakar et al., J Chem. Soc. Perkin Trans, I, 1171–1176, 1982).

For the synthesis of (N)-methanocarba-G (24) (Scheme 4), coupling under Mitsunobu conditions proceeds with a yield comparable to that of the pyrimidines. As reported in a similar case, only the desired N-9 isomer (34%) is obtained with virtually no detection of the N-7 isomer. The conversion of the 2-amino-6-chloro intermediate into the 6-0-benzyl derivative 23 facilitates the one-step removal of all protective groups in the generation of the guanine base (Rodriguez et al., Tetrahedron Lett., 34:6233–6236, 1993; Rodriguez et al., J Med. Chem., 37:3389–3399, 1994).

The (N)-methanocarba nucleoside analogs may also be incorporated into short oligodeoxynucleotides (ODNs). Standard double helices exist in the classic B-DNA form, in which all sugars have a Southern conformation, or in the A-DNA form, wherein the sugars have a N-conformation. During formation of DNA/RNA heteroduplexes, the A-form, typical of RNA, is dominant. The expected thermodynamic stability resulting from the preorganization of the pseudosugar rings into the Northern conformation, typical of A-DNA, is evident by the increase in melting temperature ($T_m$) of the corresponding DNA/RNA heteroduplex containing the (N)-methanocarba T.

The 2'-deoxy-methanacarbanucleosides or derivatives thereof, or pharmaceutically acceptable esters or salts of these compounds, may be incorporated into a pharmaceutically acceptable carrier for administration to an individual having a herpes virus infection. Contemplated routes of administration include topical, oral, intravenous, intramuscular and subcutaneous. Nonlimiting examples of particularly preferred nucleoside analog compositions for topical administration include creams, lotions, gels, salves, sprays, dispersions, suspensions, pastes and ointments.

For oral administration, the deoxynucleoside analogs may be provided as a tablet, aqueous or oil suspension, dispersible powder or granule, emulsion, hard or soft capsule, syrup or elixir. Compositions intended for oral use may be prepared according to any method known in the art for the manufacture of pharmaceutical compositions and may include one or more of the following agents: sweeteners, flavoring agents, coloring agents and preservatives. Tablets may contain the active compound in admixture with non-toxic pharmaceutically acceptable excipients including inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets may be uncoated or coated by known methods to delay disintegration and absorption in the gastrointestinal tract and thereby provide a sustained action over a longer period of time. For example, a time delay material such as glyceryl monostearate may be used.

Formulations for oral use may also be presented as hard gelatin capsules wherein the active ingredient is mixed with an inert solid diluent, such as calcium carbonate, calcium phosphate or kaolin, or as soft gelatin capsules in which the active ingredient is mixed with water or an oil medium, such as peanut oil, liquid paraffin or olive oil.

Aqueous suspensions may contain the active ingredient in admixture with excipients suitable for the manufacture of aqueous suspensions. Such excipients include suspending agents, dispersing or wetting agents, preservatives, coloring agents and sweetening agents.

The (N)-methanocarba 2'-deoxynucleoside analogs for parenteral administration may be in the form of a sterile injectable preparation, such as a sterile injectable aqueous or oleaginous suspension. This suspension may be formulated according to methods well known in the art using suitable dispersing or wetting agents and suspending agents. The sterile injectable preparation may also be a sterile injectable solution or suspension in a non-toxic parenterally-acceptable diluent or solvent, such as a solution in 1,3-butanediol. Suitable diluents include, for example, water, Ringer's solution and isotonic sodium chloride solution. In addition, sterile fixed oils may be employed conventionally as a solvent or suspending medium. For this purpose, ally bland fixed oil may be employed including synthetic mono or diglycerides. In addition, fatty acids such as oleic acid may likewise be used in the formation of injectable preparations.

The pharmaceutical compositions may also be in the form of oil-in-water emulsions. The oily phase may be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions may also contain sweetening and flavoring agents.

The antiherpetic compositions of the invention may additionally employ adjunct components conventionally found in pharmaceutical compositions in their art-established fashion and at their art-established levels. Thus, for example, the compositions may contain additional compatible pharmaceutically active materials for combination therapy (such as supplementary antimicrobials, antipruritics, astringents, local anesthetics or anti-inflammatory agents), or may contain materials useful in physically formulating various dosage forms of the present invention, such as excipients, dyes, perfumes, thickening agents, stabilizers, skin penetration enhancers, preservatives or antioxidants. For assistance in formulating the compositions of the present invention, one may refer to Remington's Pharmaceutical Sciences, 15th ed., Mack Publishing Co., Easton, Pa. (1975) the entire contents of which are hereby incorporated by reference.

Therapy is initiated as early as possible following the onset of signs and symptoms. The administration route, amount administered and frequency of administration will vary depending on the age of the patient, condition to be treated, and severity of the condition. Contemplated amounts, dosages and routes of administration for various herpes virus infections are similar to those established for the antiherpetic agent acyclovir which is also a nucleoside analog. Detailed information relating to administration and dosages of acyclovir may be found in the Physician's Desk Reference, 47th edition, pp. 844–850, 1993 and in Hayden et al., "Antiviral Agents" in Basic Principles in the Diagnosis of Infectious Diseases, pp. 271–274), the entire contents of which are hereby incorporated by reference.

Briefly, contemplated amounts of (N)-2'-deoxy-methanocarba-nucleoside analogs for oral administration to treat initial genital herpes range from about 100 mg to about 300 mg about every 4 hours, five times daily for about 10 days (500–1,500 mg/day) or until there is a significant improvement in the condition. For chronic suppressive therapy for recurrent disease, between about 300 mg and about 500 mg is orally administered twice a day for up to about 12 months (600–1,000 mg/day). For treatment of VZV, EBV and CMV, between about 10 mg/kg and about 50 mg/kg is administered four times a day for about 5 days (about 2,800–14,000 mg/day). For topical administration to HSV skin lesions and for treatment of HSV keratoconjunctivitis, a topical preparation containing about 50 mg nucleoside analog per gram of preparation is applied in an amount sufficient to adequately cover all lesions. The topical preparation is applied every 3–6 hours 4–6 times daily for about 7 days or until the lesions have disappeared (about 300 mg/day). The dose size per application will vary depending upon the total lesion area, but should approximate a one-half inch ribbon of preparation per four square inch surface area. For intravenous administration to treat HSV-1 and HSV-2, about 5 mg/kg is infused at a constant rate over 1 hour, every 8 hours (15 mg/kg/day) for about 7 days (about 1,050 mg/day). For intravenous administration to treat VZV, about 10 mg/kg is infused at a constant rate over 1 hour, every 8 hours for about 7 days in adult patients (about 2,100 mg/day). For IV administration to treat Herpes Zoster, about 5–10 mg/kg /8 h is administered for about 5 days (about 1,050–2,100 mg/day).

The nucleoside analogs locked in the N conformation can also be incorporated into oligodeoxynucleotides (ODNs) to increase the thermal stability of the ODN with its target RNA. This observation has implications in targeted gene therapy. An ODNT containing (N)-locked oligonucleosides targeted to a particular gene can be introduced into a cell and will bind to its target RNA. The increased stability of the DNA/RNA heteroduplex makes the RNA unavailable for translation into its corresponding protein.

All chemical reagents were commercially available. Melting points were determined on a Mel-Temp II apparatus (Laboratory Devices) and are uncorrected. Column chromatography was performed on silica gel 60, 230–400 mesh (Merck) and analytical thin layer chromatography (TLC) was performed on Analtech Uniplates silica gel GF. Proton and $^{13}$C-NMR spectra were recorded on a Bruker Model AC-250 instrument at 250 and 62.9 MHz, respectively. Spectra were referenced to the solvent in which they were run (7.24 ppm for $CDCl_3$). Following the norm for reporting NMR data in nucleosides, the identity of protons and carbons on the pseudosugar ring (carbocyclic moiety) are indicated by numbers with primes. Positive-ion fast-atom bombardment mass spectra (FABMS) were obtained on a VG 7070E mass spectrometer at an accelerating voltage of 6 kV and a resolution of 2000. Glycerol was used as the sample matrix and ionization was effected by a beam of xenon atoms. UV spectra were recorded in a Shimadzu Model TV-2101PC spectrometer. Elemental analyses were performed by Atlantic Microlab, Inc., Norcross, Ga.

SYNTHESIS OF (N)-2'-DEOXY-METIANOCARBA-ADENOSINE

The reaction steps for the synthesis of (N)-2'-deoxy-methanocarba-adenosine are described in Examples 1–10 and summarized in Schemes 1 and 2.

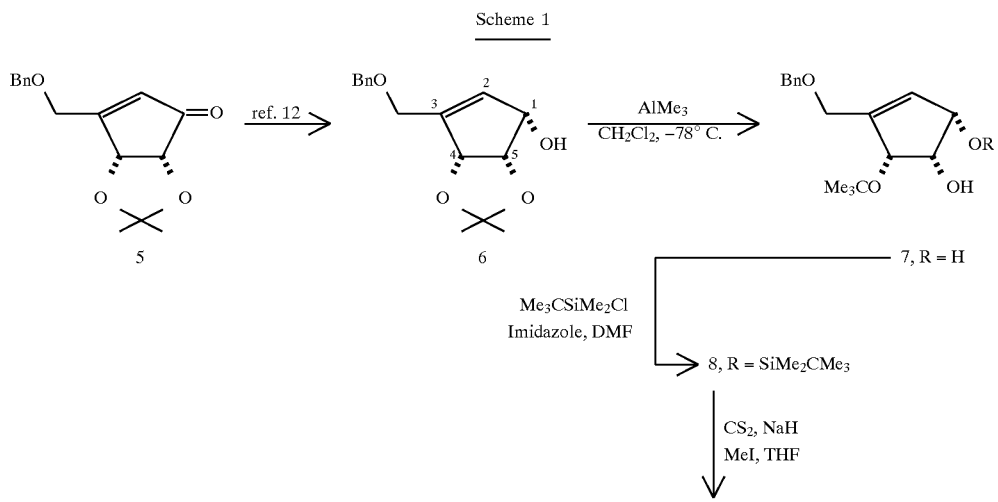

-continued
Scheme 1

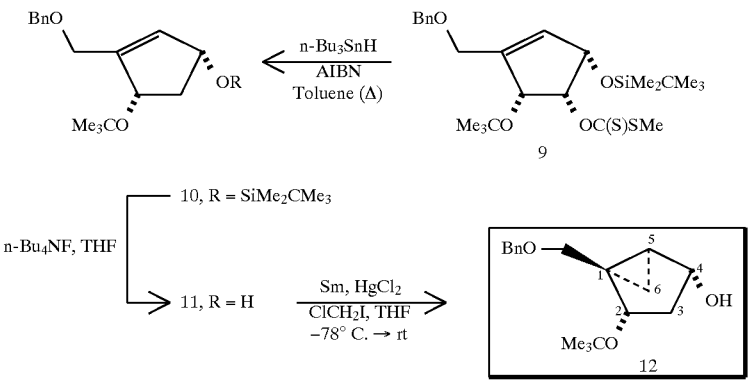

Scheme 2

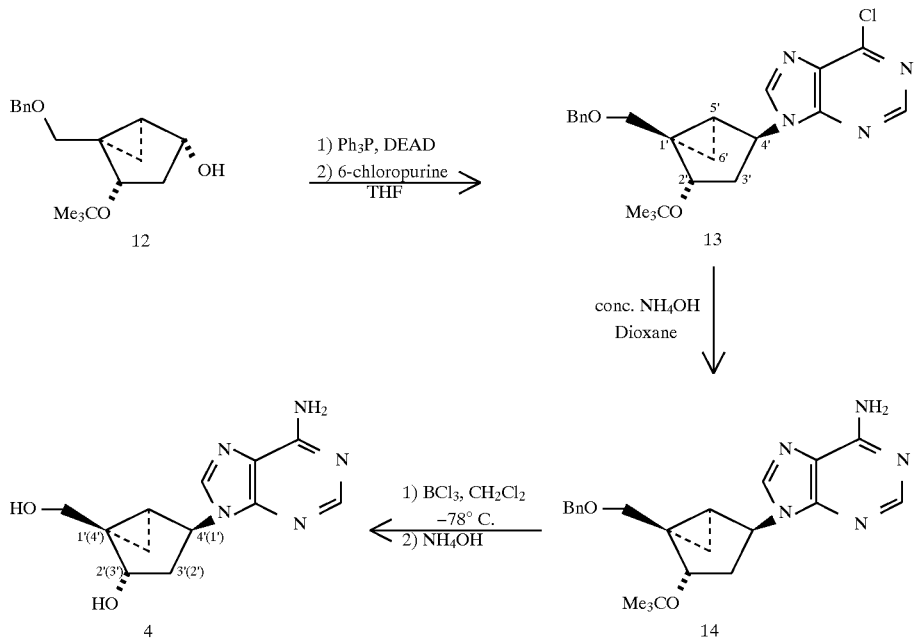

EXAMPLE 1

(1S,4R,5S)-3-r(Benzloxymethyl1-4,5-O-isopyopylidene-2-cyclonenten-1-ol (6)

This compound was prepared from compound 5 according to the procedure of Marquez et al. (J Org. Chem., 53:5709, 1988).

EXAMPLE 2

A solution of 6 (0.61 g, 2.20 mmol) was stirred in anhydrous $CH_2Cl_2$ (25 ml) at −78° C. and treated with a solution of trimethylaluminum in toluene (2 M, 7.8 ml, 15.6 mmol). The reaction was allowed to reach room temperature and stirring was continued for 18 hours. The reaction was again cooled to −78° C. and quenched by very slowly adding 10 ml of an aqueous saturated solution of $NH_4Cl$. Upon reaching room temperature, the resulting suspension was filtered and the solid cake was washed with 25 ml $CHCl_3$. The filtrate was collected and extracted with $CHCl_3$ (3×50 ml), and the combined organic extract was washed with water (50 ml), dried over $Na_2SO_4$ and concentrated under vacuum. The crude product was purified by flash column chromatography over silica gel with a 0–50% gradient of ethyl acetate in hexane as eluate to give 0.349 g (54%) of compound 7 as a thick oil. $^1H$ NMR ($CDCl_3$) δ7.20–7.40 (m, 5 H, Ph), 5.85 (br s, 1 H, H-2), 4.50 (m, 3 H, H-i, $PhCH_2O$), 4.42 (d,J=5.4 Hz, 1H, H-4), 4.15 (t,J=5.4 Hz, 1 H, H-5), 4.06 (br s, 2 H, $PhCH_2OCH_2$), 1.25 (s, 9 H, $C(CH_3)_3$); $^{13}C$ NMR ($CDCl_3$) δ141.55, 137.96, 132.26, 128.38, 127.77, 127.69, 75.50, 74.17, 73.42, 72.76, 70.86, 66.11, 28.13. Anal. calculated for $C_{17}H_{24}O_4$: C, 69.83; H, 8.27. found: C, 69.57; H, 8.27.

EXAMPLE 3

(1 S,4R,5S)-1-(tert-Butyldimethylsilyloxy)-3-[(Benzyloxy)methyl-4-tert-butyloxy-5-hydroxy-2-cyclopentene (8)

A solution of 7 (8.04 g, 27.5 mmol) and imidazole (7.05 g, 103.55 mmol) in anhydrous DMF (80 ml) was mixed with tert-butyldimethylsilyl chloride (6.70 g, 44,45 mmol). The mixture was stirred at room temperature under a blanket of argon for 40 min and quenched by the slow addition of water (100 ml). The reaction mixture was extracted with ethyl acetate (3×100 ml), and the combined organic extract was washed with brine (2×100 ml) and dried over $Na_2SO_4$. The solvent was evaporated and the product was purified by flash column chromatography over silica gel with a 0–10% gradient of ethyl acetate in hexane as eluant to give 9.77 g of pure 8 as an oil; $^1H$ NMR ($CDCl_3$) δ7.20–7.40 (m, 5 H, Ph), 5.75 (br s, 1 H, H-2), 4.50 (m, 3 H, H-1, $PhCH_2O$), 4.35 (d, J=5.2 Hz, 1 H, H-4), 4.10 (m. 3 H, H-5, $PhCH_2OCH_2$), 1.25 (s, 9 H, $C(CH_3)_3$, 0.90 (s, 9 H, $SiC(CH_3)_3$, 0.1 (s, 6 H, $Si(CH_3)_2$; $^{13}C$ NMR ($CDCl_3$) δ 143.20, 138.11, 130.21, 128.36, 127.79, 127.63, 74.54, 74.47, 73.76, 72.85, 72.45, 66,65, 28.29, 25,88, 18.30, 1.22. Anal. calculated for $C_{23}H_{38}O_4Si$-0.5$H_2O$:C, 66.46; H, 9.46. found: C, 66.41; H, 9.31.

EXAMPLE 4

(1S,4R,5S)-1-(tert-Butyldimethylsilyloxy)-3-[(Benzyloxy)methyl]-4-tert-butyloxy-5-[(methylthio)thiocarbonyloxy-2-cyclopentene (9)

A solution of 8 (9.77 g, 24.02 mmol) in anhydrous THF (100 ml) was treated with carbon disulfide (10.2 ml, 168.8 mmol). The mixture was stirred at 100° C. for 5 min, and NaH (80% suspension in oil, 2.2 g, 73.3 mmol) was added in portions, followed by stirring at room temperature for 30 minutes. Methyl iodide (19.5 ml, 313.2 mmol) and the mixture was stirred for 30 minutes. The reaction mixture was cooled to 0° C. and excess NaH was destroyed by the slow addition of water. The organic layer was separated and the aqueous layer was extracted with ethyl acetate (3×100 ml). The combined organic extract was dried over $Na_2SO_4$ and concentrated under vacuum. The crude product was purified by flash column chromatography over silica gel using a 0–5% gradient of ethyl acetate in hexane to give 9.83 g (82.4%) of pure 9 as an oil.; $^1H$ NMR ($CDCl_3$) δ7.20–7.40 (m, 5 H, Ph), 6.30 (t, J=5.3 Hz, 1 H, H-5), 5.80 (br s, 1 HI H-2), 4.70 (d,J=5.3 Hz, 1 H, H-4), 4.50 (m, 3 H, H-i, $PhCH_2O$), 4.15 (br s, 2 H, $PhCH_2OCH2$), 2.50 (s, 3 H, $SCH_3$), 1.20 (s, 9 H, $C(CH_3)_3$, 0.85 (s, 9 H, $SiC(CH_3)_3$, 0.00 and 0.01 (singlets, 6H, $Si(CH_3)_2$); $^{13}C$ NMR ($CDCl_3$) δ 216.09, 142.71, 138.03, 130.53, 128.38, 127.86, 127.69, 83.03, 74.51, 73.33, 72.97, 72.68, 66.21. 28.19, 26.00, 18.50, 18.03, 1.56. Anal. calculated for $C_{25}H_{40}O_4S_2Si$-0.25$H_2O$: C, 59.90; H, 8.10; S, 12.77. found: C, 59.84; H, 8.10; S, 12.72.

EXAMPLE 5

(1 S ,4R)-1-(tert-Butyldimethylsilyloxy)-3-[(Benzyloxy)methyl]-4-tert-butyloxy-2-cyclopentene (10)]

A solution of 9 (9.82 g, 19.76 mmol) and azobis(isobutyronitrile) (AIBN, 2.(,14 g, 12.42 mmol) in anhydrous toluene (100 ml) was heated to ca. 50° C. under a blanket of argon, and treated slowly with tri-n-butylin hydride (22 ml, 81.8 mmol). The mixture was heated at 120° C. in an oil bath for 1.5 hours, then cooled to room temperature. The solvent was evaporated and the crude product was purified by flash column chromatography over silica gel with a gradient of 0–5% ethyl acetate in hexane to give 10 (5.94 g, 77%) as an oil; 'H NMR ($CDCl_3$) δ 7.30–7.60 (m, 5 H, Ph), 5.75 (br s, 1H, H-2), 4.60 (distorted triplet, 1 H, H-4), 4.50 (AB multiplet, 2 H $PhCH_2O$), 4,41 (distorted triplet, 1 H. H-i), 4.10 (br s, 2 H, $PhCH_2OCH$ ), 2.66 (dt, J=13.2, 7.2 Hz, 1 H, H-5$_a$), 1.60 (dt,J=13.2, 5.5 Hz, 1H, H-Sb), 1.20 (s, 9H, $C(CH_3)_3$, 0.90 (s, p,H, $SiC(CH_3)_3$, 0.05 (s, 6H, $Si(CH_3)_2$); $^{13}C$ NMR ($CDCl_3$) δ143.83, 132.31, 127.77, 127.53, 74.01, 73.43, 73.26, 72.77, 66.52, 45.97, 28.56, 25.89, 18.14, 1.14. Anal. calculated for $C_{23}H_{38}O_3Si$·0.5$H_2O$: C, 69.12; H, 9.83. found: C, 69.21; H, 9.71.

EXAMPLE 6

(1S,4R)-3-[(Benzyloxymmethyl1-4-tert-butyloxy-2-cyclopenten-1-ol (11)

A solution of 10 (4.82 g, 12.36 mmol) in anhydrous THF (80 ml) was treated with a solution of tetrabutylammonium fluoride in THF (1 M, 51 ml), and the resulting mixture was stirred at room temperature overnight. The solvent was evaporated and the remaining residue was treated with water and extracted with ethyl acetate (3×100 nl). The combined organic extract was washed with brine (2×100 ml) and dried over $Na_2SO_4$. The solvent was removed under reduced pressure and the crude product was purified by flash column chromatography over silica gel using a gradient of 50–66 % ethyl acetate t6 give 11 (3.152 g, 92%) as a clear oil; $^1H$ NMR ($CDCl_3$) δ7.30–7.40 (m, 5 H, Ph), 5.90 (br s, 1 H, H-2), 4.60 (m, 1 H, H-4), 4.50 (AB multiplet, 2 H, $PhCH_2CO$), 4.45 (m, 1 H, H-i), 4.10 (br s, 2 H, $PhCH_2OCH_2$), 2.70 (dt,J=14.2, 7.2 Hz, 1 H, H-$_a$), 1.95 (br s, 1 H, OH), 1.57 (dt, J=14.2, 3.8 Hz, 1 H, H-5$_b$), 1.20 (s, 9 H, $C(CH_3)_3$; $^{13}C$ NMR ($CDCl_3$) δ145.49, 138.13, 132.39, 128.35, 127.76, 127.61, 74.44, 73.95, 73.48, 72.77, 66.42, 45,21, 28.48. Anal. calculated for $C_{17}H_{24}O3$-0.75$H_2O$: C, 70.43; H, 8.86. Found: C, 70.62; H, 8.54.

EXAMPLE 7

(1R,2S,4R,5S)-1-[(Benzloxymethyl]-2-tert-butyloxy-4-hydroxybicyclo[3.1.0] hexane (12)

Samarium metal (2.30 g, 15.29 mmol) was placed in a flask and dried with a flame under a stream of argon. anhydrous THF (10 ml) and a solution of mercuric chloride (0.40 g, 1.47 mmol) in 3 ml THF were added and the mixture was stirred for 10 min prior to the addition of a solution of alcohol 11 (1.0 g, 3.61 mmol) in THF (10 ml). The reaction mixture was cooled to −78° C. and treated with chloroiodomethane (1.15 ml, 15.71 mmol). The resulting mixture was continuously stirred starting at −78° C. and allowed to reach ambient temperature during the night. The following day, the reaction was quenched with a saturated solution of $K_2CO_3$ (50 ml) and extracted with ether (3×75 ml). The combined organic extract was washed with brine (2×75 ml), dried over $Na_2SO_4$, filtered and evaporated to dryness. The residue was purified by flash column chromatography over silica gel using a gradient of 0–50% ethyl acetate in hexane to give 12 (1.01 g, 96%) as a colorless oil; $^1H$ NMR ($CDCl_3$) δ 7.30–7.40 (m, 5 H, Ph), 4.50 (AB q, J=12 Hz, 2 H, $PhCH_2O$), 4.35 (m, 1 H, H-2), 4.25 (t, J=8.1 H, 1 H, H-4), 3.92 (AB d, J=10.2 Hz, 1 H, $PhCH_2OCHH$), 2.93 (AB d, J=10.2 Hz, 1 H, $PhCH_2OCH\underline{H}$), 2.18 (dt, J=13.1, 7.6 Hz, 1 H, H-3), 1.50 (m, 2 H, H-$^3$b, OH), 1.15 (m, 11 H, H-5, H-6$_{endo}$, $C(CH_3)_3$), 0.42 (dd, J=7.7, 5.6 Hz, 1 H, H-6$_{exo}$); $^{13}C$ NMR ($CDCl_3$) δ 128.34, 127.73, 127.58, 72.88, 71.27, 70.23, 69.33, 38.31, 33.20, 28.52, 26.52, 6.31. Anal. calculated for $C_{18}H_{26}O_3$·0.25$H_2O$: C, 73.31; H, 9.06. found: C, 73.34; H, 8.98.

EXAMPLE 8

(1R,2S,4S,5S)-1-[(Benzyloxy)methyl-2-tert-butyloxy-4-(6-chloro-9-purinyl)-bicyclo[3.1.0]hexane (13)

A stirred solution of triphenyl phosphine (0.42 g, 1.60 mmol) in anhydrous THF (5 ml) was treated with diethyl azodicarboxylate (DEAD, 0.26 ml, 1.64 mmol) at room temperature. After 20 min, a suspension of 6-chloropurine (0.248 g, 1.60 mmol) in anhydrous TIF (15 ml) was added and 20 min later the mixture became homogeneous. A solution of alcohol 12 (0.31 g, 1.06 mmol) in THF (10 ml) was then added and the resulting mixture was stirred at room temperature for 72 hours. The solvent was removed under reduced pressure and the crude product was purified by flash column chromatography over silica gel using a gradient of 0–50% ethyl acetate in hexane to give 13 (0.263 g, 58%) as a solid, mp 112°–113° C.; $^1$H NMR (CDCl$_3$) δ 9.10 (s, 1 H, H- 2), 8.70 (s, 1 H, H-8), 7.30–7.40 (m, 5 H, Ph), 5.19 (d,J=5.9 Hz, 1 H, H-4'), 4.60 (m, 3 H. H-2', PhCH$_2$O), 4.05 (AB d,J=9.9 Hz, 1 H, PhCH$_2$OCHH), 3.05 (AB d, J=9.9 Hz, 1 H, PhCH$_2$OCHH), 1.85 (m, 2 H, H-3'$_{a,b}$), 1.55 (dd,J=8.5, 3.8 Hz, 1 H, H-6'$_{endo}$), 1.05 (m, 10 H, H-5', C(CH$_3$)$_3$), 0.72 (dd,J=8.2, 6.4 Hz, 1 H, H-6'exo). anal. calculated for C$_{23}$H$_{27}$ClN$_4$O$_2$·0.5H$_2$O: C, 63.36; H, 6.47; N, 12.85. found: C, 63.34; H, 6.48; N, 12.88.

EXAMPLE 9

(1R,2S,4S,5S)-1-[(Benzyloxy)methyl]-2-tert-butyloxy-4-(6-amino-9-purinyl)-bicyclo[3.1.0lhexane (14).

A solution of 13 (0.202 g, 0.47 mmol) in dioxan (15 ml) was mixed with concentrated ammonium hydroxide (10 ml) and heated to 65° C. in a pressure bottle. After 14 hours, the solvent was removed under reduced pressure and the crude prodact purified by flash column chromatography over silica gel using ethyl acetate to give '14 (0.146 g, 76%) as an oil; $^1$H NMR (CDCl$_3$) δ 8.70 (s, 1 H, H-2), 8.30 (s, 1 H, H-E8), 7.30–7.40 (m, 5 H, Ph), 6.20 (br s, 2 H, NH$_2$), 5.10 (d,J=6.1 hz, 1 H, H-4'), 4.60 (m, 3 H, H-2', PhCH$_2$O), 4.10 (AB d, J=9.9 Hz, 1 H, PhCH$_2$OCHH), 3.10 (AB d, J=9.9 Hlz, 1 H, PhCH$_2$OCHH), 1.75 (m, 2 H, H-3'$_{a,b}$), 1.55 (m, 1 H, H-6'$_{endo}$), 1.05 (m, 10 H, H-5', C(CH$_3$)$_3$, 0.72 (m, 1 H, H-6'$_{exo}$); $^{13}$C NMR δ 155.17, 152.08, 149.46, 139.79, 137.93, 128.53, 127.83, 119.51, 73.37, 73.24, 71.04, 70.29, 54.48, 38.75, 33,53, 28.37, 24.:3,0, 10.37. Anal. calculated for C$_{23}$H$_{28}$N$_5$02H$_2$O: C, 65.07; H, 7.12; N, 16.49. Found: C, 64.89; H, 6.85; N, 16.12.

EXAMPLE 10

(1 R,2S,4S,5S)-1-Hydroxymethyl-2-hydroxM-4-(6-amino-9-purinyl)bicyclo[3.1.0]hexane (4).

A stirred solution of 14 (0.130 g; 0.319 mmol) in anhydrous CH$_2$Cl$_2$ (10 ml) and under a blanket of argon was cooled to $-78°$ C. and treated with a solution of BCl$_3$ (1 M in CH$_2$Cl$_2$, 3 ml). After 4 hours, the reaction was quenched with ca. 1 ml methanol and allowed to reach room temperature. The solvent was removed under reduced pressure and the residue was co-evaporated with additional methanol (4×5 ml). The final residue was dissolved in 30 ml methanol and neutralized to pH 12 with 25% aqueous ammonium hydroxide. The volatiles were removed and the crude residue purified by reverse phase chromatography (Baker octadecyl C-18) using a gradient of 0–20% methanol in water to give 4 (0.058 g, 70%) as a solid, mp 259°–261° C. (dec.); [α]$_D^{25}$- 16.90 (c 0.13 DMF); $^1$H NMR (D$_2$O) δ8.20 (s, 1 H, H-2), 8.00 (s, 1 H, H-8), 4.80 (d, J=6.7 Hz, 1 H, H-4'), 4.70 (t, J=8.5 Hz, 1 H, H-2'), 4.00 (AB d, J=12.3 Hz, 1 H, C HHOH, 3.31 (AB d, J=12.3 Hz, 1 H. CHHOH, 2.01 (dd, J=14.8, 7.9 Hz, 1 H, H-3'$_a$), 1.70 (m, 2 H, H-3'$_b$, H-5'), 0.91 (dd, J=5.7, 3.9 Hz, 1 H, H-6'$_{endo}$), 0.72 (distorted triplet, 1 H, H-6'exo); $^{13}$C NMR (D$_2$O/methanol-d$_6$) δ 156.50, 153.23, 149.86, 141.18, 120.10, 72.01, 63.57, 56.38, 37.70, 36.21, 26.50, 10.60; FAB MS m/z (relative intensity) 262 (MH+, 100), 136 (b+2H, 58). Anal. calculated for C$_{12}$H$_{15}$N$_5$,O$_2$·0.33H$_2$0: C, 53.93; H, 5.90; N, 26.21. Found: C, 53.78; H, 5.66; N, 26.04.

SYNTHESIS OF (N)-METHANOCARBA-THYMIDINE, URIDINE, GUANOSINE AND CYTIDINE

The synthetic steps described below in Examples 11–17 are summarized in Schemes 3 (thymidine, uridine and cytidine analogs) and 4 (guanosine analog).

Scheme 3

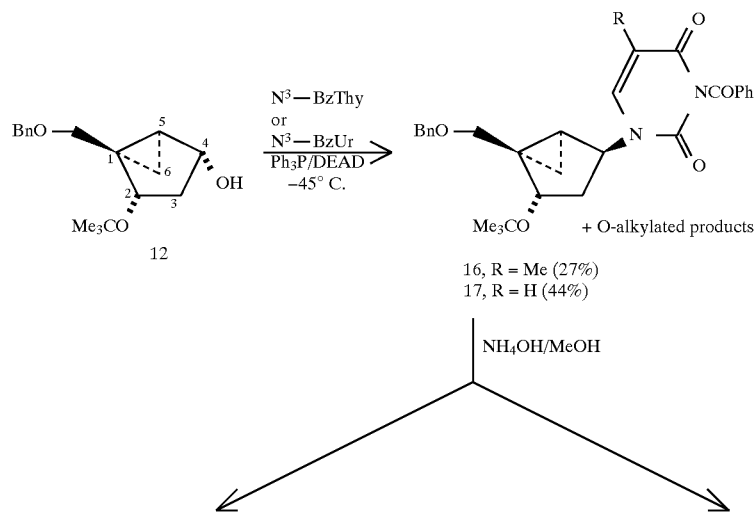

-continued
Scheme 3

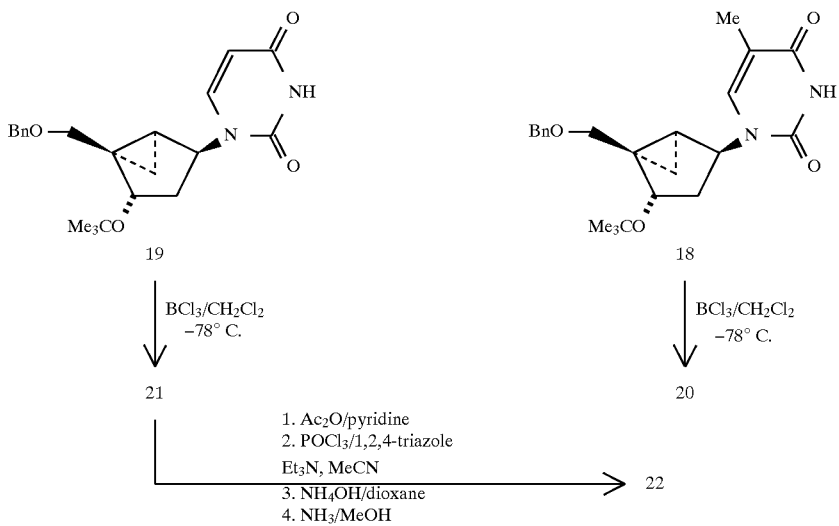

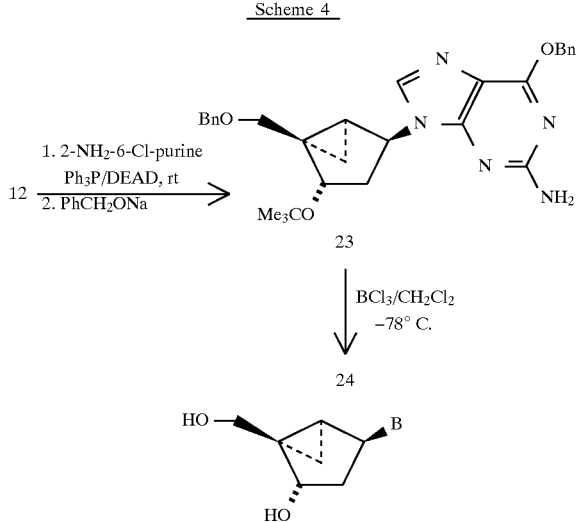

20, B = thymine [(N)-methanocarba-T]
21, B = uracil   [(N)-methanocarba-U]
22, B = cytosine [(N)-methanocarba-C]
24, B = guanine  [(N)-methanocarba-G]

EXAMPLE 11

(1 R,2S,5S)-1-[[(Benzyloxy)methyl]-2-tert-butyloxy-4-(5-methyl-2,4-( 1H,3H-dioxopyrimidin-1-yl)bicyclo[3.1.0]hexane (18)

A solution of triphenylphosphine (4.18 g, 15.93 mmol) in anhydrous THF (40 ml) was treated with DEAD (2.75 g, 15.8 mmol) and stirred under argon at 0° C. for 30 min. The solution was cooled to −45° C. and a suspension of $N^3$-benzoylthymine (3.0 g, 13.0 mmol) in THF (50 ml) was added, followed by a solution of carbocyclic alcohol 12 (1.89 g, 6.50 mmol) in THF (30 ml). The reaction mixture was stirred at −45° C. for 2 hours and allowed to reach room temperature overnight. The solvent was evaporated at reduced pressure and the residue was purified first by flash chromatography (silica gel, 0%–40% ethyl acetate in hexane) to give a mixture of N- and O-alkylated products, which were re-chromatographed (silica gel, 0% to 5% ether in $CH_2Cl_2$ to give 0.87 g (27%) of the desired N-alkylated product 16 as a semisolid and 1.30 g (40%) of the O-alkylated product as an oil. The N-alkylated product (16) was dissolved in methanol (200 ml), treated with concentrated $NH_4OH$ (15 ml) and stirred at room temperature overnight. The solvent was evaporated under reduced pressure and the crude product was purified by flash column chromatography (silica gel, 0%–50% ethyl acetate in hexane) to give 18 (0.25 g, 78%) as a white solid, mp 158°–160° C.; $^1$H NMR (CDCl$_3$) δ 8.20 (br s, 1 H, NH), 7.88 (d,J=1.1 Hz, 1 H, H-6), 7.60–7.35 (m, 5 H, ArH), 4.93 (d,J=6.8 Hz, 1 H, H-4'), 4.62-4.42 (m, 3 H, H-2', PhCH$_2$O), 4.13 (AB d, J=9.9Hz, 1 H, PhCH$_2$OCHH), 3.09 (AB d,J=9.9 Hz, 1 H, PhCH$_2$OCHH, 1.90-1.60 (m, 2 H. H-3'$_{a,b}$), 1.48 (s, 3 H, CH$_3$), 1.25 (m, 1 H, H-5'), 1.15 (s, 9 H, C(CH$_3$)$_3$), 0.92 (m, 1 H, H-6'$_{endo}$), 0.65 (dd,J=8.6,6.3 Hz, H-6'$_{exo}$). Anal. calculated for $C_{23}H_{30}N_2O_4 \cdot 0.33$ H$_2$O:C, 68.30; H, 7.65; N, 6.93. Found: C, 68.11; H, 7.67; N, 6.68.

EXAMPLE 12

(1 R,2S,4S,5S)-1-(Hydroxymethyl-2-hydroxy-4-(5-methyl-2,4-(1H,3H)-dioxopyrimidin-1-yl)bicyclo[3.1.0]hexane (20)

A solution of 18 (0.60 g, 1.50 mmol) in dry CH$_2$Cl$_2$ (100 ml) was cooled to −78° C. under argon and treated with BCl$_3$ (1 M in CH$_2$Cl$_2$, 13 ml). The reaction mixture was stirred at −78° C. for 4 hours and the solvent was removed under reduced pressure. The residual material was treated with several portions of methanol (4×20 ml) and evaporated to dryness. The crude product was purified by flash chromatography (silica gel. 0–25% methanol in CH$_2$Cl$_2$) to give 0.291 g (76%) of 20 as a solid. This material was further purified be reverse phase chromatography (Baker octadecyl C-18) using a gradient of 0–5% methanol in water to give 0.231 g of a white crystalline solid, mp 239°–241° C.; $[\alpha]_D^{25}$=+47° (c 0.28, MeOH); $^1$H NMR (Me$_2$SO-d$_6$) δ 11.20 (s, 1 H, NH), 7.91 (s, 1 H, H-6), 5.01 (t,J=4.8 Hz, 1 H, OH), 4.70 (d,J=6.8 Hz, 1 H, H-4'), 4.65-4.50 (m, 2 H, OH, H-2'), 4.07 (dd,J=11.2,4.9 Hz, 1 H. CHHOH), 3.05 (dd,J=11.2,4.5 Hz, 1 H, CHHOH), 1.80-1.45 (m, 2 H, H-3'$_{ab}$), 1.22 (dd,J=8.4,3.5 HFz, 1 H, H-5').

EXAMPLE 13
(1R,2S,4S,5S)-1-[(Benzyloxy)methyl]-2-ter t-butyloxy-4-(2,4-(1H,3H)-dioxypyrimidin-1-yl)bicyclo[3.1.0]hexane (19)

Following a similar procedure for the synthesis of 18, the desired N-alkylated product (17, 0.360 g, 44%) was hydrolyzed to compound 19 (0.27 g, 98%) which was obtained as a foam; $^1$H NMR (CDCl$_3$) δ 8.25 (br s, 1 H, NH), 8.15 (d, J=8.0 Hz, 1 H, H-6), 7.60-7.25 (m, 5 H, ArH), 5.32 (dd,J= 8.0, 2.4 Hz, H-5), 4.95 (d,J=6.6 Hz, 1 H, ]H-4'), 4.60-4.45 (m, 3 H, H-2', PhCH$_2$O), 4.15 (AB d,J=9.8 Hz, 1 H, PhCH$_2$OCHH, 3.10 (AB d,J=9,8 Hz, 1 H, PhCH$_2$OCHH, 1.88-1.60 (m, 2 H, H-3'$_{ab}$), 1.23 (dd,J=8.5, 3.7 Hz, 1 H. H-5'), 1.15 (s, 9 H, C(CH$_3$)$_3$, 0.95 (dd,J=5.8, 3.9 Hz, 1 H, H-6'$_{endo}$), 0.70 (dd,J=8.3, 6.1 Hz, H-6'$_{exo}$) Anal. calculated for C$_{22}$H$_{26}$N$_2$O$_4$: C, 69.09; H, 6.85; N, 7.32. Found: C, 68.99; H, 6.89; N, 7.39.

EXAMPLE 14
(1R,2S,4S,5S)-1-(Hydroxymethyl)-2-hydroxy-4-(2,4-(1H, 3H)-dioxopvrimidin-1-yl)bicyclor3.1.Olhexane (21)

After a similar deblocking procedure used for the preparation of 20, the crude material was purified by column chromatography (silica gel, 25% isopropanol in CH$_2$Cl$_2$), and following recrystallization from MeOH/ether, 0.069 g (93%) of 21 was obtained as a khite solid, mp 157°–159° C.; [α]$_D^{25}$=+51°(c 1, MeOH): $^1$H NMR (Me$_2$SO-d$_6$) δ 11.20 (s, 1 H, NH), 7.91 (d,J=8.0 Hz, 1 H, H-6), 5.51 (dd,J=8.0, 2,2 Hz, 1 H, H-5), 4.90 (br s, 1 H, OH), 4.52 (d,J=6.9 Hz, 1 H, H-4'), 4.51 (t,J=8.5 Hz, 1 H, H-2'), 4.05 (d,J=11.3 Hz, 1 H, CHHoH), 3.35 (br s, 2 H, OH), 3.10 (d,J=11.3 Hz, 1 H, CH HOH), 1.75 (dd,J=14.7, 8.0 Hz, 1 H, H-3'$_a$), 1.58 (m, 1 H, H-$^{3'}{}_a$), 1.24 (dd.J=8.4,3.4 Hz, 1 H, H-5'), 0.75 (irregular t, 1 H, H-$^{6'}{}_{endo}$), 0.55 (dd,J=8.4,5.3 Hz, 1 H, H-6'$_{exo}$); $^{13}$C NMR (CH$_3$OH-d$_4$) δ 9.28, 24.05, 36.51, 37.78, 55.43, 61.31, 69.08, 100.93, 141.80, 150.89, 163.18; FAB MS (m/z, relative intensity) 239 (MH+, 85), 113 (b +2 H, 100). Anal. calculated for C$_{11}$H$_{14}$N$_2$O$_4$·0.25H$_2$O: C, 54.43; H, 6.02; N, 11.54. Found: C, 54.47; H, 5.88; N, 11.23.

EXAMPLE 15
(1R, 2S, 4S, 5S)-1-(Hydroxymethyl)-2-hydroxy-4-(4-amino-2-(1H)-oxolpyrimidin-1yl)bicyclo[3.1.Olhexane (22)

Uracil nucleoside 21 (0.527g, 2.21 mmol) was stirred at room temperature 1b)r 2 hours in the presence of acetic anhydride (20 ml) and pyridine (30 ml). The reaction mixture was concentrated under reduced pressure and excess pyridine was removed by azeotropic distillation first with toluene and then with diethyl ether. The residue was recrystallized from isopropanol/ether to give 0.544 g (first crop) and 0.086 g (seco:nd crop) of the diacetate of 21 (88% yield) as a white solid, mp 126°–127° C.; $^1$H NMR (CDCl$_3$) δ8.55 (s, 1 H, NH), 7.60 (d,J=8.0 Hz, 1 H, H-6), 5.72 (dd,J=8.0, 2.2 Hz, 1 H, H-5), 5.55 (t,J=8.4 Hz, 1 H, H-2'), 5.05 (d,J=7.5 Hz, 1 H, H-4'), 4.51 (d,J=12.1 Hz., 1 H. CHHOH), 3.81 (d,J= 12.1 Hz, 1 H. CHHOH), 2,25 (d,J=15.7,8.4 Hz, 1 H, H-3'$_a$), 1.80 (m, 1 H, H-$^{3'}{}_b$), 1.45 (dd,J=8.7,3.9 Hz, 1 H, H-5'), 1.08-0.88 (m, 2 H, H-6'). Anal. calculated for C$_5$H$_{28}$N$_2$O$_6$: C, 55.90; H, 5.63; N, 8.69. Found: C, 55.81; H, 5.59; N, 8.60.

An ice-cold solution of 1,2,4-triazole (0.54 g, 7.76 mmol) in CH$_3$CN (30 ml), maintained under argon, was treated with POCl$_3$ (0.71 ml, 7.76 mmol) and stirred cold for 15 min. The diacetate (0.25 g, 0.776 mmol) and triethylamine (1.1 ml, 0.76 mmol) were added and the reaction was stirred at room temperature overnight. The solvent was removed under reduced pressure and the resulting orange residue was dissolved in CH$_2$Cl$_2$ (100 ml), then extracted with water (3×75 ml) and brine (75 ml). The solution was dried over MgSO$_4$ and filtered. The filtrate was reduced to dryness under vacumn and the residue was purified by flash column chromatography (silica gel, 10% MeOH in ethyl acetate). The collected fractions were evaporated and the solid material triturated with a mixture of ethyl acetate and petroleum ether to give the solid triazole intermediate (0.138 g, 46%). This material was dissolved in a mixture of dioxane (16 ml) and concentrated NH$_4$OH (4 ml) and stirred overnight at room temperature. The solvent was removed under reduced pressure and the residue was purified by flaesh column chromatography (silica gel, 5% MeOH in CH$_2$Cl$_2$) to give the semisolid diacetate of 22 (0.105 g, 92%) which was immediately dissolved in saturated methanolic ammonia (35 ml) and stirred overnight at room temperature. The solvent was removed under reduced pressure and the residue was redissolved and reconcentrated from CHCl$_3$ (3×50 ml). The residue was warmed with CHCl$_3$ and let stand at room temperature. The resulting solid was collected by filtration to give 0.038 g (65%) of 22. An analytical sample of 22 was obtained by recrystallization from MeOH to give white crystals, mp 283°–290° C.; [α]$_D^{25}$=+74° (c 1, MeOH); $^1$H NMR (Me$_2$SO-d$_6$) δ 7.90 (d,J=7.3 Hz, 1 H, H-6), 7.00 (br d, 2 H, NH$_2$), 5.65 )d,J=7.3 Hz, 1 H, H-5), 4.88 (t,J=5.0 Hz, 1 H, OH), 4.75 (d,J=6.5 Hz, 1 H, H-4'), 4.60-4.40 (m, 2 H, OH, H-2'), 4.05 (dd,J=11.4, 5.2 Hz, 1 H, CHHOH), 3.12 (dd,J= 11.4, 5.0 Hz, 1 H, CHHOH), 1.72-1.43 (m, 2 H, H-3',b), 1.20 (dd,J=8.4, 3.5 Hz, 1 H, H-5'), 0.75 (irregular t, 1 H, H-6'$_{endo}$), 0.55 (dd,J=8.2,5.2 Hz, 1 H, H-6'$_{exo}$); $^{13}$C NMR (Me$_2$SO-d$_6$) δ 9.33 24.41, 36.44, 38.16, 55,75, 61.50, 69.18, 93.18, 142,34, 155,48, 165.14; FAB MS (m/z, relative intensity) 238 (MH$^+$, 100), 112 (b+2H, 60). Anal. calculated for C$_{11}$H$_{15}$N$_3$O$_3$: C, 55.69; H, 6.37; N, 17.71. Found: C, 55.54; H, 6.34; N, 17.64.

EXAMPLE 16
(1 R,2S,4S,5 S)-1- [(Benzyloxy)methyll-2-tert-butyloxy-4-[2-amino-6-(benzyloxy)-9-purinyl)bicoclor3.1.0Olhexane (23)

A stirred solution of triphenylphosphine (1.37 g, 5.22 mmol) in anhydrous THF (30 ml) was treated with DEAD (0.91 g, 1.64 mmol) at room temperature. After 30 min, a suspension of 2-amino-6-chloropurine (0.248 g, 1.60 mmol) in anhydrous TlHF (15 ml) was added and 30 min later a solution of carbocyclic alcohol 12 (0.50 g, 1.72 mmol) in THF (30 ml) was added. The resulting mixture was stirred at room temperature for 20 h. The suspension was filtered and the filtrate was concentrated under reduced pressure. The crude product was purified by flash column chromatography (silica gel, 0–50% ethyl acetate in hexane) to give the 6-chloro intermediate (0.26 g, 34% as a foam). The compound was reacted with a freshly made solution of PhCH$_2$ONa (prepared from 10 ml benzyl alcohol and 0.30 g of Na) arid stirred at room temperature for 30 min. The mixture was quenched with water arid extracted with CH$_2$Cl$_2$ (2×75 ml). The combined organic extract was washed with water until the pH of the washings was neutral, dried over MgSO$_2$ and concentrated under reduced pressure. The residue was purified by flash column chromatography (silica gel, 0–50% ethyl acetate in hexane to give 0.215 g (72%) of 23 as a solid, mrip 180°–181° C.; $^1$H NMR (CDCl$_3$) δ 8.50 (s, 1 H, H-8), 7.20–7.50 (m, 10 H, ArH), 5.60 (AB q, 12.1 Hz, 2 H, PhCH$_2$O) 5.20 (br s, 2 H, NH2), 4.95 (d,J=6.0 Hz, 1 H, H-4'), 4.63 (t,J=8.3 H, 1 H, H-2'), 4.55 (AB q, J=12.1 Hz, 2 H, PhCH$_2$O), 4.06 (AB d,J=9.9 Hz, 1 H, PhCH$_2$0CHHO), 3.03 (AB d,J=9.9 Hz, 1 H, PhCH$_2$0CHHO), 1.92-1.67 (m, 2 H, H-3'$_{a,b}$), 1.49 (dd,J=

8.4,3.7 Hz, 1 H, H-5'), 1.07 (s, 9 H, C(CH$_3$)$_3$), 1.00 (dd,J= 5.7,4.0 Hz, 1 H, H-6'$_{endo}$), 0.68 (dd,J=8.0,6.2 Hz, 1 H, H-6'$_{exo}$). Anal. calculated for C$_{30}$H$_{35}$N$_5$O$_3$: C, 70.15; H, 6.87; N, 13.64. Found: C, 70.03; H, 6.92; N, 13.55.

EXAMPLE 17

(1R,2S,4S,5 S)-1-(Hydroxymethyl)-2-hydroxy-4-[2-amino-1.9-dihydro-6H-6-oxopurin-9-yl)bicyclor3.1.0]hexane (24)

A stirred solution of 23 (0.130 g, 0.253 mmol) in CH$_2$Cl$_2$ (10 ml) was maintained under argon, cooled to −78° C. and treated with BCl$_3$ (1.0 M in hexane, 2 ml). The solution was stirred at that temperature for 4 hours, quenched with MeOH 92 ml) and allowed to reach room temperature. The solvent was removed and additional amounts of MeOH 94×5 ml) were added and evaporated successively. The crude product was purified by reverse phase chromatography (Baker octadecyl C-18) using a gradient of 0–10% MeOH in water to give 0.054 g (77%) of 24 as a foam; [α]$_D^{25}$=+18° (c 0.4, DMF); $^1$H NMR (Me$_2$SO-d$_6$) δ 10.50 (br s, 1 H, NH), 8.00 (s, 1 H, H-8), 6.45 (s, 2 H, NH$_2$), 4.92 (t,J=4.9 Hz, 1 H, OH), 4.68 (m, 1 H, H-2'), 4.61 (d,J=6.0 Hz, 1 H, H-4'), 4.05 (dd,J=14.3, 7.5 Hz, 1 H, H-3'j, 1.70-1.50 (m, 1 H, H-$^{3'}$$_b$), 1.45 (dd,J=8.1,3.3 Hz, 1 H, H-5'), 0.84 (t,J-4.3 Hz, 1 H, H-6'$_{endo}$), 0.59 (dd,J=8.0,5.4 Hz, 1 H, H-6'$_{endo}$); $^{13}$C NMR (Me$_2$SO-d$_6$) δ9.29, 24.96, 35,87, 37.86, 53.45, 61.49, 69.30, 116.56, 135.19, 150.61, 153.44, 156.89; FAB MS (nzlz, relative intensity) 278 (MH+, 100), 152 (b+2H, 57); high resolution FAB MS, MH+calculated 278.1253, found 278.1251. Because the value for nitrogen was off in the conventional analysis, the purity of the sample (99.6%) was assessed by HPLC (column: Altex ODS, 250×4.6 mm; mobile phase: 75% CH$_3$CN, 10 mM phosphate buffer; χ=255 nm).

EXAMPLE 18

X-ray analysis of compound 4

Figure 3:
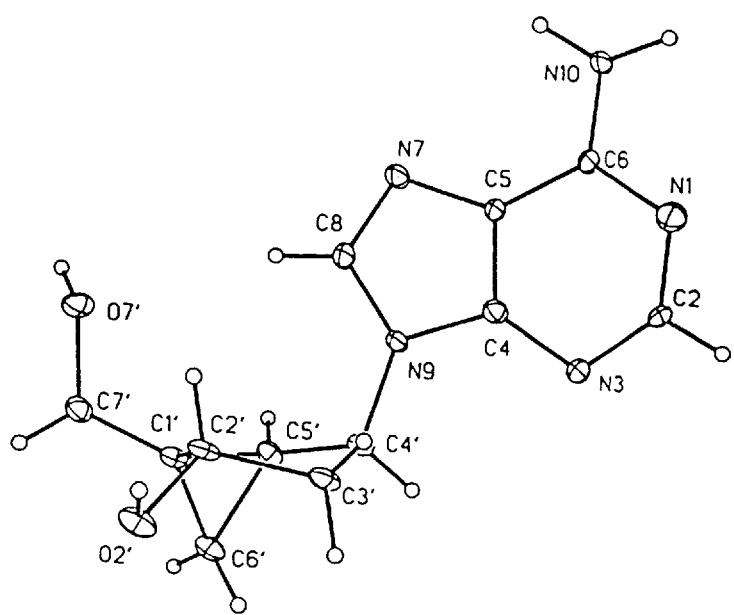
FIG. 3 is a perspective view of compound 4 as found in the crystal structure. C2' and C3' correspond, respectively, to C3' and C2' in a pentofuranose ring.

X-ray crystallographic data was generated for compound 4·2H$_2$O (C$_{12}$H$_{15}$N$_5$O$_2$·2H$_2$O), FW=297.32, mp 259°–261° C. (dec.). Triclinic, space group P1, a=6.1740(11), b=8.270 (2), c=14.760(2) Å, α=94.280(10), β=100.250(10), γ=102.240(10)°, V=719.8(2) Å$^3$, Z=2, D,=1.372 mg mm$^{-3}$, λ(CuKα)=1.54178 Å, $\mu$=0.881 mm$^{-1}$, F(000)=316, T=223 (2)'K. Final residuals were R=0.0454 for 20,40 reflections I>2σ(I$_o$). The atomic coordinates [x 10$^4$] and equivalent isotropic displacement parameters [Å$^2$×10$^3$] for compound 4 are shown in Table 1. A perspective view of the structure computed from the final relative atomic coordinates is shown in FIG. 3.

The unit cell of the crystal contained two nearly identical molecules (A and B) which differ only in terms of the value of the torsion angle γ that determines the orientation of the free primary hydroxy group. The pseudorotational parameters calculated from the crystal structure were as follows: P=339.250°, v$_{max}$=31.80°, χ=−167.6° (molecule A); and P=342.78°, v$_{max}$=30.46°, χ=−154.8° (molecule B). These values are in perfect agreement with a 2'-exo/3'-endo conformation with a theoretical value of P=342'. The value of X for both molecules corresponds to the characteristic and orientation about the glycosyl bond. Also, the values of important dihedral ang]les that would determine the multiplicity of the pseudoanomeric proton signal in solution agree with the 'H NMR data. The measured angles for H5'-C5'-C4'-H4'[-80.02° (molecule A) and −82.82° (molecule B)], H4'-C4'-C3'-H3'$_\beta$[90.29° (molecule A) and 93.70° (molecule B)], and H4'-C4'-C3'-H3'a [−30.90° (molecule A) and −27.10° (molecule B)] explain why a doublet is observed for the pseudoanomeric proton of 4, and confirms that the compound has the identical conformation in solution as in the solid state.

TABLE 1

|  | x | y | z | U (eq) |
|---|---|---|---|---|
| N(1A) | 1128(8) | −1508(6) | 7392(3) | 39(1) |
| C(2A) | 2613(11) | −1764(7) | 6858(4) | 39(2) |
| N(3A) | 3765(8) | −725(6) | 6382(3) | 33(1) |
| C(4A) | 3302(9) | 798(7) | 6487(4) | 28(1) |
| C(5A) | 1832(9) | 1258(6) | 7013(4) | 25(1) |
| C(6A) | 692(9) | 29(6) | 7470(3) | 28(1) |
| N(7A) | 1790(8) | 2926(6) | 6960(3) | 33(1) |
| C(8A) | 3244(10) | 3411(7) | 6423(4) | 35(1) |
| N(9A) | 4222(7) | 2185(5) | 6118(3) | 28(1) |
| N(10A) | −804(8) | 265(6) | 7998(3) | 37(1) |
| C(1'A) | 6364(8) | 4839(7) | 4734(4) | 27(1) |
| C(2'A) | 4397(9) | 3576(7) | 4148(4) | 29(1) |
| C(3'A) | 4639(9) | 1887(7) | 4460(4) | 32(1) |
| C(4'A) | 5863(9) | 2277(7) | 5499(4) | 32(1) |
| C(5'A) | 7254(9) | 4027(7) | 5566(4) | 29(1) |
| C(6'A) | 8636(9) | 4392(8) | 4822(4) | 34(1) |
| O(2'A) | 4436(7) | 3645(5) | 3185(2) | 39(1) |
| C(7'A) | 6316(9) | 6642(7) | 4800(4) | 35(1) |
| O(7'A) | 4271(6) | 6845(5) | 5095(3) | 39(1) |
| N(1B) | −2839(8) | −6956(6) | 8507(3) | 36(1) |
| C(2B) | −4437(11) | −7472(7) | 8998(4) | 42(2) |
| N(3B) | −5610(8) | −6609(6) | 9421(3) | 39(1) |
| C(4B) | −5066(8) | −5000(6) | 9288(3) | 24(1) |
| C(5B) | −3542(8) | −4297(6) | 8772(3) | 24(1) |
| C(6B) | −2301(9) | −5341(6) | 8384(3) | 28(1) |
| N(7B) | −3460(7) | −2607(5) | 8759(3) | 29(1) |
| C(8B) | −4919(9) | −2352(6) | 9263(4) | 30(1) |
| N(9B) | −5963(7) | −3727(5) | 9601(3) | 25(1) |
| N(10B) | −657(7) | −4794(6) | 7929(3) | 29(1) |
| C(1'B) | −7206(9) | −1092(6) | 11070(4) | 28(1) |
| C(2'B) | −5581(9) | −1982(7) | 11599(3) | 30(1) |
| C(3'B) | −6449(9) | −3844(7) | 11226(4) | 34(1) |
| C(4'B) | −7610(9) | −3841(7) | 10223(4) | 29(1) |
| C(5'B) | −8516(8) | −2270(6) | 10212(3) | 25(1) |
| C(6'B) | −9689(9) | −1893(7) | 10955(4) | 32(1) |
| O(2'B) | −5327(7) | −1680(6) | 12577(3) | 43(1) |
| C(7'B) | −6393(9) | 754(7) | 11074(4) | 34(1) |
| O(7'B) | −8114(7) | 1465(5) | 10584(3) | 42(1) |
| O(1S) | 8162(7) | 4833(6) | 2414(3) | 43(1) |
| O(2S) | 177(7) | 2296(5) | 2131(3) | 42(1) |
| O(3S) | 1297(7) | 7485(5) | 3518(3) | 46(1) |
| O(4S) | −1117(7) | −4(6) | 3346(3) | 51(1) |

EXAMPLE 9

Conformational analysis of N-2'-deoxy-methanocarba-T

The complete definition of the conformation of a nucleoside usually involves the determination of three groups of structural parameters: (a) the orientation about thle glycosyl bond as syn or anti, which is more precisely defmed by the value of the torsion angle χ; (b) the orientation of the hydroxymethyl group determined by the value of the torsion angle γ; and (c) the deviation from planarity of the sugar ring measured by the angle of pseudorotation P. The pseudorotational angle P is calculated according to equation (1)

$$tan\ P=(v_4+v_1)-(v_3+v_0)/2\ sin\ v_2\ (sin\ 36° +sin\ 72°)$$  (1)

The endocyclic torsion angles v$_0$–v$_4$ were measured directly from the X-ray structures. For the cyclopentane ring, these angles correspond to equivalent torsion angles as defined for a sugar moiety in Saenger et al., ibid. The torsion angles χ (pseudoglycosyl bond) and y correspond, respectively, to C$_2$-N$_1$-C$_4$'-C$_5$, and HO-CH$_2$-C$_1$-C$_2$. These torsion angles are equivalent to C$_2$-N$_1$-C$_1$-O$_4$, and O$_5$-C$_5$,-C$_4$,-C$_3$', in pyrimidine nucleotides.

The x-ray coordinates of (N)-methanocarba-T (20) (Altmann et al., Tetrahedron Lett., 35:2331–2334, 1994) and (S)-methanocarba-T (25) (Altmann et al., Tetrahedron Lett., 35:7625–7628, 1994) were exported into the CaChe Scientific Work System (Oxford Molecular) version 4.0 using Allinger's standard MM2 force field parameters. The optimization method employed was the Block Diagonal Newton Raphson with a convergence criterion equal to 0.001 kcal/mol. The corresponding energies wi re calculated (Table 2) after locking the geometry of the torsion angles $\chi$ (pseudoglycosyl bond) and y (exocyclic $CH_2OH$ bond) (Saenger, ibid., pp. 9–28). From these structures, a conformational analysis was performed for each compound by allowing the torsion angles $\chi$ and $\gamma$ to rotate 360° in increments of 15°. This generated an optimized potential energy map for each compound from which the global energy minima conformations were identified (Table 2). In both instances, the global energy minima corresponded to conformations where the torsion angle X favors a syn-orientation that facilitates an intramolecular hydrogen bond between the C2 carbonyl and the hydro:y of the $CH_2OH$ group. As seen in Table 2, the X-ray structure of (S)-methanocarba.-T (25) showed a similar preference and, in terms of conformational parameters and energy, is very close to the calculated global minimum.

Conversely, the X-ray structure of (N)-methanocarba-T (20) differed significantly from the global minimum since in prefers, instead, the anti-conformation. The X-ray conformation is about 3 kcal/mole higher than the global minimum conformation. However, such energy difference corresponds almost entirely to hydrogen bonding. The hydrogen bond energy was estimated, in both cases, by measuring the depth of the lowest energy well from the surrounding low energy conformations without hydrogen bonding. The energy difference between the global minimum in the syn-conformation and the lowest possible anti-configuration for (N)-methanocarba-T is also 3 kcal/mole. For (S)-methanocarba-T, the corresponding difference between syn and anti conformation approaches 4 kcal/mole, also due to hydrogen bonding.

TABLE 2

|  | X-ray Structure | Global Minima (H-Bond) | Minima (anti) | H-bond | $E_{syn/anti}$ |
|---|---|---|---|---|---|
| (N)-methano-carba-T (20) | $\chi = -147°$ anti | $\chi = 30°$ syn | $\chi = -150°$ | E = 3 | E = 8 |
|  | $\gamma = 67°$ | $\gamma = 45°$ | $\gamma = 60°$ |  |  |
|  | P = 343° | P = 346° | P = 344° |  |  |
|  | E = 67.23 | E = 64.07 | E = 67.09 |  |  |
| (S)-methano-carba-T (25)[a] | $\chi = 59°$ syn | $\chi = 45°$ syn | $\chi = -135°$ | E = 4 | E = 9 |
|  | $\gamma = 56°$ | $\gamma = 60°$ | $\gamma = 60°$ |  |  |
|  | P = 190° | P = 101° | P = 190° |  |  |
|  | E = 82.92 | E = 82.65 | E = 86.62 |  |  |

[a]Molecule B for (S)-methanocarba-T: $\chi = 68°$ (syn), $\gamma = 51°$, P = 190°, E = 83.44 Kcal/mol. (molecule A was selected because its energy corresponded to almost that of the global minimum).

As expected, the differences in the values of P between X-ray and energy-minimized structures were minimal in the pseudorotational scale for each pseudorotational antipode (Table 2). For (N)-methanocarba-T, the maximum value of P was 3°, whereas for (S)-methanocarba-T this value was just 1° for either molecule, A or B, in the crystal asymmetric unit. This indicates that the ring pucker remained fundamentally unchanged. In terms of $\chi$ and $\gamma$, however, significant differences were observed between the two pseudorotational antipodes themselves and conventiornal nucleosides. Despite the fact that in both cases energetically reasonable syn or anti conformations could be achieved, the rotational barrier for $\chi$ ($E_{syn/anti}$) was 5 to 6 kcal/mole higher than for thymidine (calculated under the same conditions) with the S conformer having a higher energy barrier than the N conformer. These energy barriers correspond to values that exclude hydrogen bonding.

Figure 4:
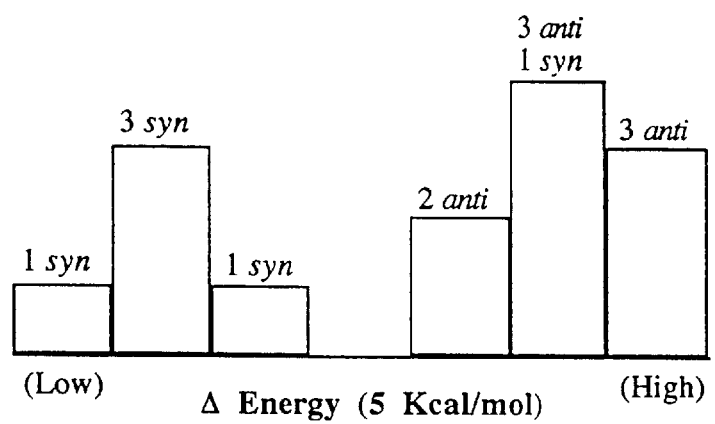
FIG. 4 is a graph showing the energy distribution of 14 rotamers of (N)-methanocarba-T wi/energies of up to 5 kcal/mole above the global minimum.
Figure 5:
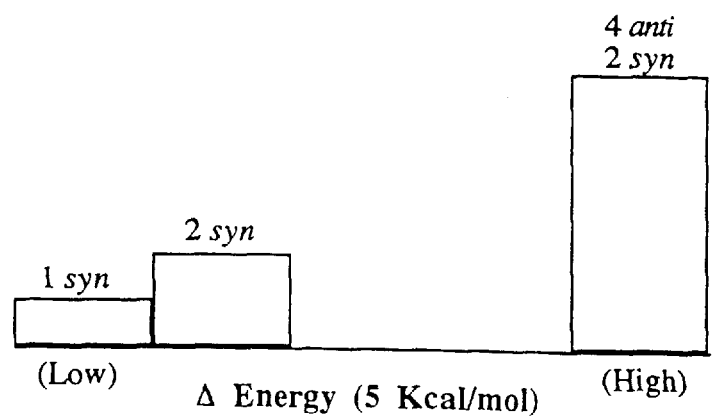
FIG. 5 is a graph showing the energy distribution of 9 rotamers of (S) methanocarba-T energies of up to 5 koal/mole above the global minimum.

Conversely, the rotational barrier for $\gamma$ was lower than for thymidine by about 2 and 1 kcal/mole, respectively, for the N and S conformers. The combination of higher energy barriers for the S conformer revealed in the potential energy map a much stiffer molecule with fewer low energy conformational states available when compared to the (N) conformer. Such stiffness can be better appreciated by comparing the distribution of energy conformations for rotamers 5 kcal/mole above the global minimum (FIGS. 4 and 5). For the N conformer, there is a wider distribution of rotamers at about 5 kcal/mole above the global minimum, whereas for the S conformer there are fewer rotamers available.

EVALUATION OF ANTIVRAL ACTIVITY OF (N)-2'-DEOXY-METHANOCARBA-NUCLEOSIDE ANALOGS

Compound 4, prepared according to Schemes 1 and 2, was evaluated for both its ability to be deaminated to hypoxanthine by adenosine deaminase (ADA) and its antiviral activity. Compounds 20, 21, 22, and 24 were evaluated for their antiherpetic activity. The assays and results are described in the following examples.

EXAMPLE 19

Adenosine deaminase studies of 4

Figure 6:
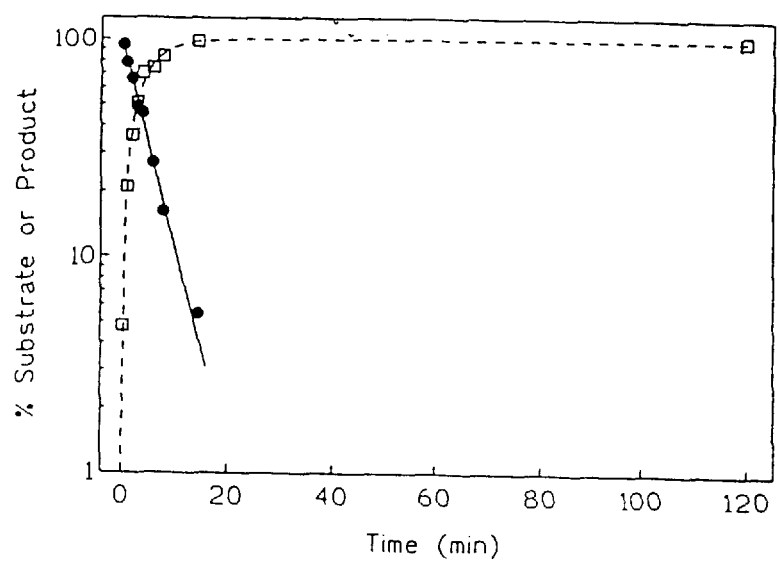
FIG. 6 is a graph illustrating the substrate disappearance and product formation from the interaction of compound 4 with adenosine deaminase (filled circles) and a hypoxanthine analog (open squares).

Compound 4 (50 $\mu$M) was incubated with 1.0 unit of ADA (Boehring,er Mannheim, Indianapolis, Ind., 2984 U/ml @ 25° C.) at 37° C. in 10 mM phosphate buffer, pH 7.1 in a volume of 1 ml. At timed intervals, 50 ll aliquots were quenched with 450 $\mu$l water containing the ADA inhibitor deoxycoformycin (4 $\mu$M). Hydrolysis kinetics of 4 were followed by high performance liquid chromatography (HPLC) with on-the-fly UV spectral characterization of all chromatographic components. HPLC conditions were as follows: pump, Waters 6000A; detector, Perkin-Elmer LC 235 Diode Array @ 260 rm, AUFS 0.05; column, Beckam/Altex 5 $\mu$ODS, 250×4.6 mm; mobile phase, $CH_3CN$ 7.5% in 0.01 M phosphate buffer, pH 7.0; flow rate, 1 ml/min. Curve fitting of the data to an exponential decay equation (y-Aexp (Bx)) for substrate disappearance and an exponential association equation (y=Aexp$^{(-Bx)}$) for the inosine analog product formation yielded the curves shown in FIG. 6. The hydrolysis rate constant (k/ADA) and $t^{1/2}$ of decay or formation were obtained using GraphPAD Inpiot curve fitting program. Compound 4 ($t_R$=9.9 min) was chromatographically pure under the isocratic conditions described, and the ADA hydrolysis product ($t_R$=5.4 min) appeared as a less lipophilic peak.

The use of ADA is very selective for the deamination of racemic 3, where only the enantiomer with a configuration equivalent to that of the "natural" nucleoside was deaminated by the enzyme (Rodriguez et al., J Med. Chem., 37:3389, 1994). Because the synthesis of 4 was chiral, it was expected to undergo complete deamination by ADA which was, indeed, the case. As seen in FIG. 3, deamination of 4 to the hypoxantie nucleoside was complete after 30 min with a $t_{1/2}$ of 3.2 min.

EXAMPLE 20

Antiviral assay

Antiviral testing of nucleoside analogs was performed on various herpes viruses. Two days prior to use, human foreskin fibroblasts (BFF) were trypsinized, counted, seeded onto six well plates and incubated at 37° C., 5% $CO_2$, 90% relative humidity. Virus was diluted in Modified Eagle's Medium (MEM) containing 10% fetal bovine serum (FBS) at a desired concentration to give 20–30 plaques/well. Media was aspirated from the wells and 0.2 ml virus +0.2 ml media was added to each well in duplicate. Plates were incubated for 1 hour with shaking every 15 minutes. After the incubation, equal volumes of 1% agarose and the diluted nucleoside analog were combined and applied to each well in a 2 ml volume. The plates were incubated for three days and cells were stained with a 1.5% solution of neutral red. After 4–6 hours, the stain was aspirated and plaques were counted using a stereomicroscope at 10×magnification.

The results for compounds 4 (Schemes 1–2) and 20 (Scheme 3) are shown in Tables 3 and 4, respectively. Compounds 25 and 26 are (S)-methanocarba-T and (±)-(carba-T), respectively. (±)-carba-T was kindly provided by Dr. Y. Fulmer Shealy, Southern Research Institute, Birmingham, Ala.

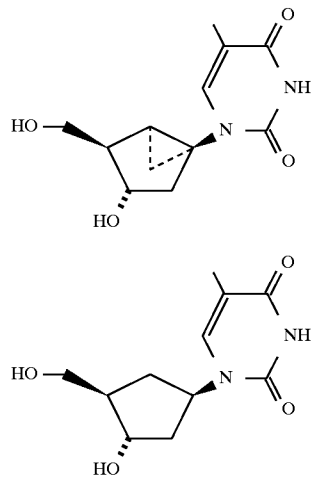

TABLE 3

| Virus[a] | Compound 4 Host Cell[b] | $EC_{50}$[c] | $CC_{50}$[d] | SI[e] | Positive Control Drug[f] | $EC_{50}$[c] |
|---|---|---|---|---|---|---|
| HSV-1 | HFF | 72.0 | >100 | >1.4 | ACV | 0.8 |
| HSV-2 | HFF | 13.9 | >100 | >7.2 | ACV | 4.0 |
| HCMV | HFF | 3.1 | >100 | >32.2 | GCV | 0.3 |
| EBV | Daudi | 1.5 | >100 | >66.7 | ACV | 0.1 |
| — | Growing HFF | — | >100 | — | ACV | 40.0 |

[a]HSV-1 = herpes simplex type 1; HSV-2 = herpes simplex type 2; HCMV = human cytomegalovirus; EBV = Epstein-Barr virus.
[b]HFF = human foreskin fibroblasts.
[c]$EC_{50}$ = inhibitory concentration in μg/mL required to reduce virus-induced cytopathogenicity (or viral capsid antigen for EBV) by 50%.
[d]$CC_{50}$ = cytotoxic concentration in μg/mL that produces 50% of cell death.
[e]SI = selectivity index ($CC_{50}/EC_{50}$).
[f]ACV = acyclovir; GCV = gancyclovir.

TABLE 4

| Compound | Virus[a] | $EC_{50}$[b] (μg/mL) | $CC_{50}$[c] (μg/mL) | SI[d] | ACV[e] ($EC_{50}$) (μg/mL) |
|---|---|---|---|---|---|
| 20 | HSV-1 | 0.01 | >20 | >2000 | 0.30 |
| " | " | 0.08[f] | >20 | >250 | 0.30[f] |
| " | HSV-2 | 0.12 | >20 | >167 | 0.80 |
| " | " | 0.43[f] | >20 | >46.5 | 1.10[f] |
| " | EBV | 0.45 | >100 | >222 | 0.10 |
| 25 | HSV-1 | >50 | >50 | 1 | 0.15 |
| " | " | >20 | >20 | 1 | 0.30 |
| " | HSV-2 | >50 | >50 | 1 | 0.60 |
| " | " | >20 | >20 | 1 | 1.10 |
| 26 | HSV-1 | >10 | >10 | 1 | 0.30 |
| " | HSV-2 | >10 | >10 | 1 | 0.80 |

[a]HSV-1 = herpes simplex type 1; HSV-2 = herpes simplex type 2.
[b]$EC_{50}$ = inhibitory concentration required to reduce the number of virus plaques by 50%.
[c]$CC_{50}$ = cytotoxic concentration that produces 50% of cell death.
[d]SI = selectivity index ($CC_{50}/EC_{50}$).
[e]ACV = acyclovir control.
[f]These values correspond to a drug pre-treated plaque reduction assay.

The results indicate a weak level of activity of compound 4 against HSV-1 and significant activity against HSV-2 (Table 3). Compound 4 also exhibited good activity against HCMV ($EC_{50}$=3.1 gg/ml). This was only ten fold less potent than gancyclovir, an established anti-herpes virus agent. However, considering that 4 was equally non-toxic to rapidly proliferating cells and stationary cells, its antiviral selectivity is superibor to that of gancyclovir which exhibited increased cytotoxicity towards rapidly dividing cells. Good anti-EBV activity ($EC_{50}$=1.5 μg/ml) was also observed which was only fifteen fold weaker than acyclovir.

Compound 20 exhibited strong activity against HSV-1 and HSV-2 (Table 4). This activity was stronger than observed with acyclovir. Compound 20 also exhibited significant anti-EBV activity, although not as strong as ACV (Table 4). In contrast, the (S)-methanocarba-T and plain (±) carba-T did not exhibit antiherpetic activity. Compounds 20, 25 and 26 were all non-toxic ($CC_{50}$>100 μg/ml) against stationary cells. The order of potency against rapidly dividing cells was (±) plain carba-T (26) ($CC_{50}$=0.65 μg/ml)>(N)-methanocarba-T (2) ($CC_{50}$=32.9 μg/ml)>(S)-methanocarba-T (25) ($CC_{50}$>100 μg/ml). Gancyclovir, used as a reference for cell cytotoxicity, showed an average $CC_{50}$ of 40.0 μg/ml in rapidly dividing HFF cells.

Table 5 provides antiherpetic data for the (N) and (S) methanocarba analogs of adenosine, cytidine, uracil and guanine. The (S) conformers of all these analcgls exhibited little, if any activity with the exception of the adenosine analog which was active against HCMV. The (N) cytidine analog was very active against HSV-1, and active against HCMV. Little activity was seen against HSV-2. The (N) uridine analog was inactive against all three viruses. The (N) guanosine analog was active against HSV-1 and HSV-2, but exhibited little activity against HCMV. The (N) adenosirte analog results are discussed in regard to Table 3. The results indicate that the (N)-methanocarba adenosine, thymidine, cytidine and guanosine analogs are effectivre antiherpetic agents.

TABLE 5

| Compound | virus[a] (host cell) | $EC_{50}$[b] (μg/ml) | $CC_{50}$[c] (μg/ml) | SI[d] | Control[e] $EC_{50}$ (μg/ml) |
|---|---|---|---|---|---|
| (S)-DMC-A | HSV-1 | >100 | >100 | 1 | ACV (0.20) |
| " | HSV-2 | >100 | >100 | 1 | ACV (0.20) |

TABLE 5-continued

| Compound | virus[a] (host cell) | EC$_{50}$[b] (μg/ml) | CC$_{50}$[c] (μg/ml) | SI[d] | Control[e] EC$_{50}$ (μg/ml) |
|---|---|---|---|---|---|
| " | HCMV | 6.4 | >100 | >15.6 | GCV (0.10) |
| " | HCMV[f] | 2.4 | >100 | >41.7 | GCV (0.20) |
| (N)-DMC-A | HSV-1 | 72.0 | >100 | >1.4 | ACV (0.80) |
| " | HSV-2 | 13.9 | >100 | >7.2 | ACV (4.0) |
| " | HCMV | 3.1 | >100 | >32.2 | GCV (0.30) |
| " | HCMV[f] | 5.6 | >100 | >17.9 | GCV (0.30) |
| (S)-DMC-C | HSV-1 | >4.0 | 14.9 | <3.7 | ACV (0.20) |
| " | HSV-2 | >4.0 | 14.9 | <3.7 | ACV (1.8) |
| " | HCMV | 88.9 | >100 | >1.1 | GCV (0.01) |
| (N)-DMC-C | HSV-1 | 0.14 | 68 | 486 | ACV (0.70) |
| " | HSV-2 | >20 | 96 | <4.8 | ACV (6.2) |
| " | HCMV | >4.0 | 8.8 | <2.2 | GCV (0.02) |
| (S)-DMC-U | HSV-1 | >20 | 59.1 | <3.0 | ACV (0.20) |
| " | HSV-2 | >20 | 59.1 | <3.0 | ACV (1.8) |
| " | HCMV | >100 | >100 | 1 | GCV (0.01) |
| (N)-DMC-U | HSV-1 | >100 | >100 | 1 | ACV (0.60) |
| " | HSV-2 | >100 | >100 | 1 | ACV (1.5) |
| " | HCMV | >100 | >100 | 1 | GCV (0.40) |
| (S)-DMC-G | HSV-1 | >20 | 75.0 | <3.7 | ACV (0.20) |
| " | HSV-2 | >20 | 75.0 | <3.7 | ACV (1.8) |
| " | HCMV | >20 | >20 | <2.3 | GCV (0.01) |
| (N)-DMC-G | HSV-1 | 4.0 | >100 | >25 | ACV (0.6) |
| " | HSV-2 | 9.9 | >100 | >10.1 | ACV (1.5) |
| " | HCMV | >20 | 64.3 | <3.2 | GCV (0.4) |

[a]HSV-1 = herpes simplex type 1; HSV-2 = herpes simplex type 2; HCMV = human cytomegalovirus.
[b]EC$_{50}$ = inhibitory concentration required to reduce virus-induced cytopathogenicity or virus plaques by 50%.
[c]CC$_{50}$ = cytotoxic concentration that produces 50% cell death.
[d]SI = selectivity index (CC$_{50}$/EC$_{50}$).
[e]ACV = acyclovir control; GCV = gancyclovir control.
[f]plaque reduction assay.

Because several adenosine analogs active against HCMV are also good inhibitors of the enzyme S-adenosylhomocysteine hydrolase (AdoHcy-ase), the activity of 4 was tested against it. The activity of 4 against AdoHcy-ase was very low (20% inhibition at a concentration of 100 μM), indicating that its antiviral activity is independent of its interaction with the enzyme. Accordingly, it is expected that 4 should be inactive against viruses which are sensitive to the inhibition of the enzyme.

EXAMPLE 21

Effect of multiple (-methanocarba-T on T$_m$

To determine the effect of multiple nucleoside analogs on the thermal stability of a RNA/DNA heteroduplex, a test sequence was synthesized corresponding to the coding region of the SV40 large T antigen (ODN, Test 1, Table 6) according to standard methods as the phosphorothioate 5'-CTTCATTTTTCTTC-3' (SEQ ID NO: 1), in which all thymines were replaced by (N)-methanocarba-Ts. This and other control ODNs indicated in Table 6 were evaluated by T$_m$ analysis on the complementary RNA target. T$_m$ was measured using the complementary RNA strand in 5 mM Na$_2$HPO$_4$, pH 7.2, 140 mM KCl, 1 mM MgCl$_2$. As seen in Table 6, the increase in thermodynamic stability of the heteroduplex due to the presence of multiple (N)-methanocarba-T nucleotides resulted in an average stabilization per substitution of about 1.3° C. relative to thymidine.

TABLE 6

| ODN | T analog[a] | C analog[a] | T$_m$[b] |
|---|---|---|---|
| Test 1 | (N)-methano-carba-T | pC | 58.5° C. |
| Control 1 | T | pC | 44.0° C. |
| Control 2 | T | 5-Me-C | <40° C. |
| Control 3 | pU | pC | 70.0° C. |

ODN = 5'-CTTCATTTTTCTTC-3';
[a]T and C positions are completely substituted with: (N)-methanocarba-T, thymidine (T), 5-propynyl-2'-deoxyuridine (pU), 5-propynyl-2'-deoxycytidine (pC), or 5-methyl-2'-deoxycytidine (5-Me-C).
[b]T$_m$ was measured using the complementary RNA strand in the buffer, 140 mM KCI/5 mM Na$_2$HPO$_4$/1 mM MgCl$_2$, pH 7.2.

The increased stability of DNA/RNA heterodupexes wherein the DNA contains one or more (N)-methanocarba-nucleoside analogs are also usefull as antisense therapeutic agents and as in situ hybridization probes for detecting a particular RNA of interest in, for example, a tissue sample. The increased stability of the resulting heteroduplex will allow hybridization to occur under more stringent conditions, thus increasing the signal to noise ratio of the desired RNA.

EXAMPLE 22

Treatment of genital herpes

An adult having an initial episode of genital herpes (HSV-2 infection) is treated with (N)-metianocarba-T, G, A or C in capsule form. A dosage amount of 200 mg is administered every four hours, five times daily for 10 days. This amount may be adjusted to reflect the potencies of the compounds as summarized in Table 5.

EXAMPLE 23

Treatment of genital or oral herpes

An individual having genital or oral herpes is treated with a topical preparation containing 50 mg of (N)-methanocarba-A, T, G, or C in a polyethylene glycol base. A sufficient amount is applied to adequately cover all lesions every 3 hours six times a day for seven days.

EXAMPLE 24

Treatment of chicken pox Burkitt's lymnhoma or cytomegalovirus inclusion disease 10 mg/kg of (N)-methanocarba-A, T, G or C (sterile lyophilized powder in Ringer's solution) is infused into an adult patient having chicken pox, Burkitt's lymphoma or cytomegalovirus inclusion disease at a constant rate over 1 hour, every 8 hours (30 mg/kg/day) for seven days.

It should be noted that the present invention is not limited to only those embodiments described in the Detailed Description. Any embodiment which retains the spirit of the present invention should be considered to be within its scope. However, the invention is only limited by the scope of the following claims.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 15 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

C T T C A T T T T T  T C T T C                                                                              1 5

What is claimed is:

1. A method of treating a herpes virus infection in an individual in need thereof, comprising the step of administering to said individual an effective herpes antiviral amount of a compound having the formula

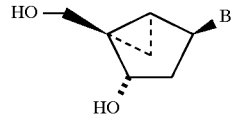

in a pharmaceutically acceptable carrier, wherein B is selected from the group consisting of adenine, thymine, cytosine and guanine.

2. The method of claim 1, wherein said herpes virus is selected from the group consisting of Herpes Simplex Virus-1, Herpes Simplex Virus-2, Epstein-Barr Virus, Cytomegalovirus and Varicella-Zoster Virus.

3. The method of claim 1, wherein said effective amount is between about 300 mg and about 15,000 mg per day.

4. The method of claim 1, wherein said administering step is topical, oral, intravenous, intramuscular or subcutaneous.

5. A pharmacutical composition comprising the compound of claim 1 in a pharmaceutically acceptable carrier.

* * * * *